US009931179B2

(12) United States Patent
Rouiller

(10) Patent No.: US 9,931,179 B2
(45) Date of Patent: Apr. 3, 2018

(54) ENDODONTIC INSTRUMENT FOR DRILLING THE ROOT CANALS OF A TOOTH

(71) Applicant: FKG DENTAIRE S.A., La Chaux-de-Fonds (CH)

(72) Inventor: Jean-Claude Rouiller, La Chaux-de-Fonds (CH)

(73) Assignee: FKG DENTAIRE S.A., La Chaux-de-Fonds (CH)

(*) Notice: Subject to any disclaimer, the term of this patent is extended or adjusted under 35 U.S.C. 154(b) by 156 days.

(21) Appl. No.: 14/930,844

(22) Filed: Nov. 3, 2015

(65) Prior Publication Data

US 2016/0051339 A1 Feb. 25, 2016

Related U.S. Application Data

(63) Continuation-in-part of application No. 13/994,162, filed as application No. PCT/CH2011/000296 on Dec. 12, 2011.

(30) Foreign Application Priority Data

Dec. 16, 2010 (CH) ...................................... 2100/10

(51) Int. Cl.
*A61C 5/02* (2006.01)
*A61C 5/42* (2017.01)
(Continued)

(52) U.S. Cl.
CPC ................. *A61C 5/023* (2013.01); *A61C 5/42* (2017.02); *C22C 19/03* (2013.01); *C22F 1/10* (2013.01)

(58) Field of Classification Search
CPC ....................................................... C22F 1/10
See application file for complete search history.

(56) References Cited

U.S. PATENT DOCUMENTS 636,359 A 11/1899 Schultz
4,019,254 A 4/1977 Malmin
(Continued)

FOREIGN PATENT DOCUMENTS

| EP | 2 272 460 A2 | 1/2011 |
| WO | 2005/070320 A1 | 8/2005 |
| WO | 2009/103444 A1 | 8/2009 |

OTHER PUBLICATIONS

International Search Report Corresponding to PCT/CH2011/000296 dated May 8, 2012.
(Continued)

*Primary Examiner* — Jessee Roe
(74) *Attorney, Agent, or Firm* — Davis & Bujold PLLC; Michael J. Bujold

(57) ABSTRACT

A method of forming a dental tool or instrument having a memorized shape. The method comprises selecting a nitinol wire having an initial transition temperature below room temperature; grinding the nitinol wire to form the dental tool or instrument so as to have a shank, located adjacent a first end, and a working area, with at least one cutting edge, located adjacent an opposite second leading end; molding the working area into a molded shape having at least one protrusion formed therein; heating the dental tool or instrument to both: a) alter the initial transition temperature of the dental tool or instrument to a final transition temperature, and b) memorize the Molded shape including the at least one protrusion so that the dental tool or instrument will automatically return to the molded shape having the at least one protrusion when at a temperature at or above the final transition temperature.

15 Claims, 15 Drawing Sheets

(51) Int. Cl.
 *C22C 19/03* (2006.01)
 *C22F 1/10* (2006.01)

(56) References Cited

U.S. PATENT DOCUMENTS

| | | |
|---|---|---|
| 4,850,867 A | 7/1989 | Senia et al. |
| 4,889,487 A | 12/1989 | Lovaas |
| 5,735,690 A | 4/1998 | Malentacca |
| 5,752,825 A | 5/1998 | Buchanan |
| 6,059,572 A | 5/2000 | Riitano |
| 6,149,501 A | 11/2000 | Farzin-Nia et al. |
| 6,494,713 B1 | 12/2002 | Pond |
| 6,579,092 B1 | 6/2003 | Senia et al. |
| 7,713,059 B2 | 5/2010 | Hof et al. |
| 7,833,017 B2 | 11/2010 | Hof et al. |
| 8,062,033 B2 | 11/2011 | Luebke |
| 8,083,873 B2 | 12/2011 | Luebke |
| 8,562,341 B2 | 10/2013 | Luebke |
| 8,647,116 B2 | 2/2014 | Becker et al. |
| 8,727,773 B2 | 5/2014 | Luebke |
| 8,876,991 B2 | 11/2014 | Luebke |
| 2002/0137008 A1 | 9/2002 | McSpadden et al. |
| 2005/0136375 A1 | 6/2005 | Sicurelli, Jr. et al. |
| 2007/0015107 A1 | 1/2007 | Mannschedel et al. |
| 2007/0054238 A1 | 3/2007 | Hof et al. |
| 2008/0057468 A1 | 3/2008 | Rosenblood et al. |
| 2008/0176191 A1 | 7/2008 | Koch et al. |
| 2010/0233648 A1 | 9/2010 | McSpadden et al. |
| 2010/0330526 A1 | 12/2010 | Pfaff et al. |

OTHER PUBLICATIONS

S.A. Thompson, "An Overview of Nickel-Titanium Alloys Used in Dentistry", International Endodontic Journal, 33, 2000, pp. 297-310.

Pelton, DiCello, Miyazaki, "Optimization of Processing and Properties of Medical-Grade Nitinol Wire" NDC, 2000, pp. 361-374.

Patrick Metrailler, "Système de détection de fatigue pour outils en alliage à mémoire de forme", École Polytechnique Fédérale de Lausanne, Feb. 8, 1999, 52 pages.

Clavel, Gotthardt, Bidaux, Van Humbeeck, Hongler and Jacot, "Conception de Dispositifs en Alliage à Mémorie de forme en Microtechnique", Yves Bellouard, Thèse No. 2308, 2000, 178 pages.

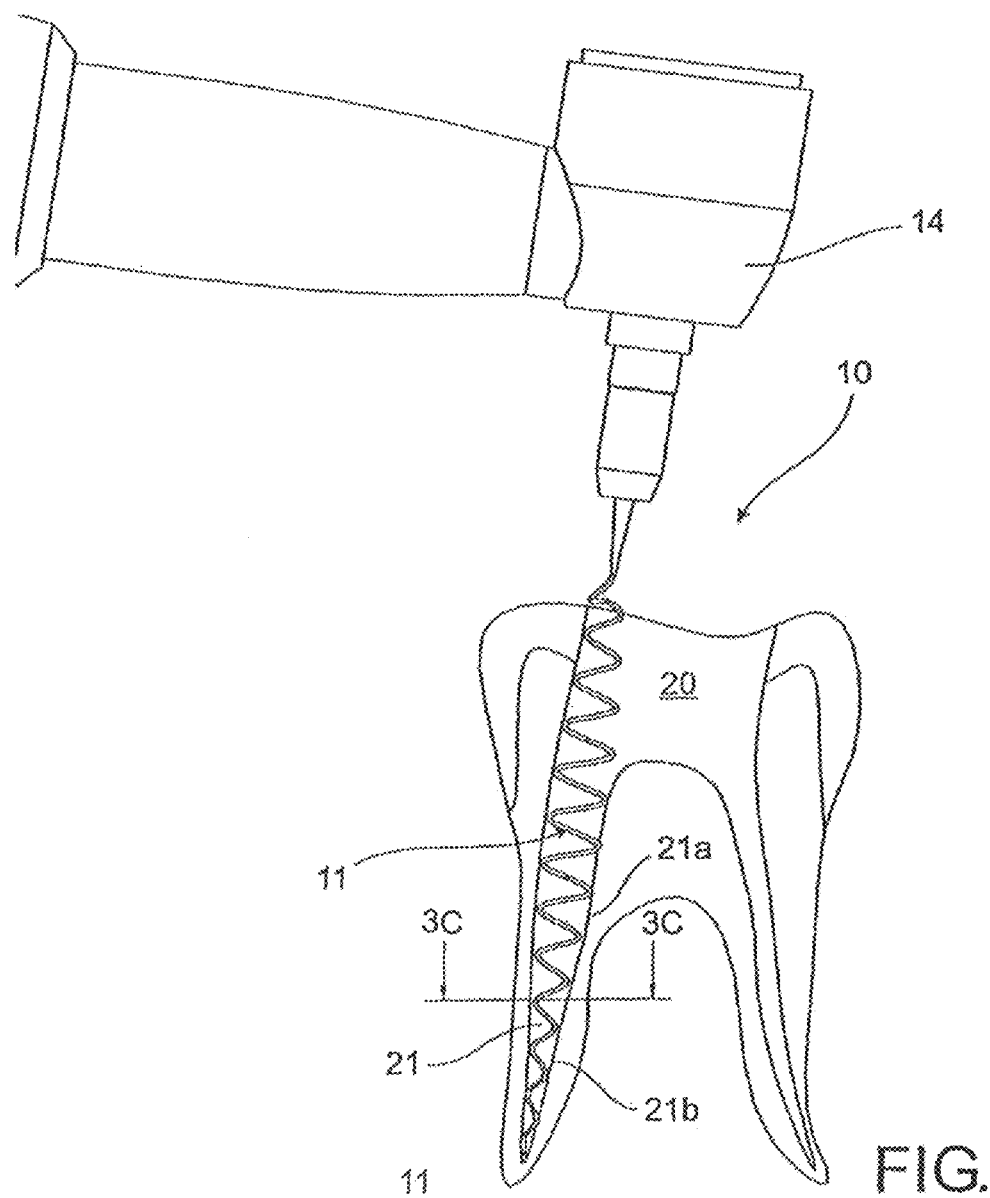
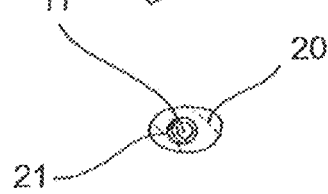
FIG. 3A
FIG. 3C

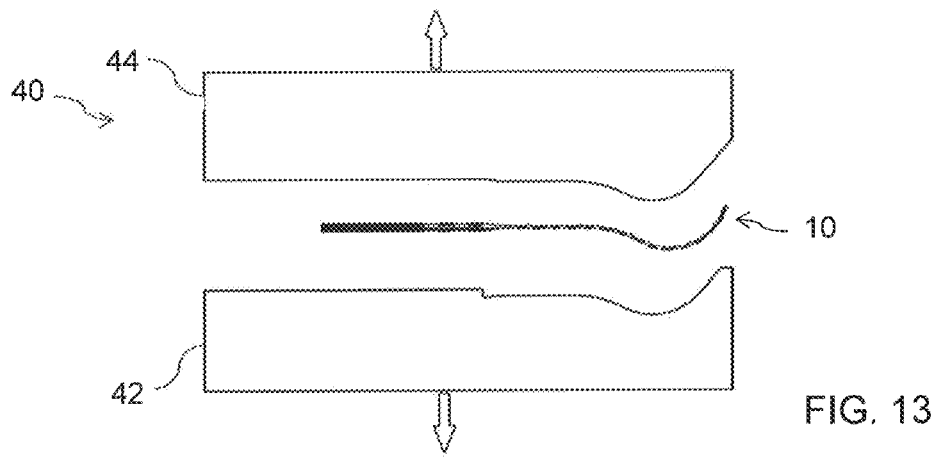
FIG. 13
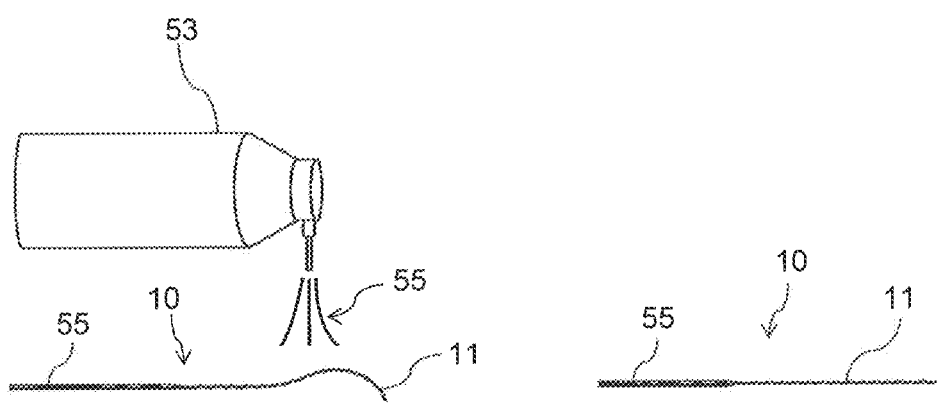
FIG. 14
FIG. 14 A
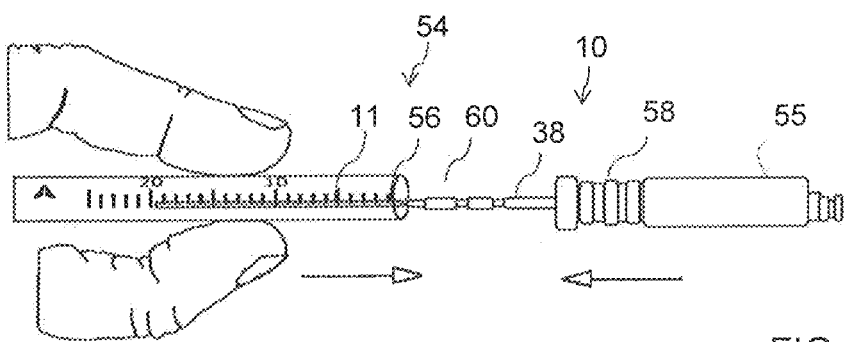
FIG. 14 B

ENDODONTIC INSTRUMENT FOR DRILLING THE ROOT CANALS OF A TOOTH

This application is a continuation in part of U.S. patent application Ser. No. 13/994,162 filed Dec. 12, 2011, which is a national stage completion of PCT/CH2011/000296 filed Dec. 12, 2011 which claims priority from Swiss Application Serial No. 2100/10 filed Dec. 16, 2010.

FIELD OF THE INVENTION

The present invention concerns an endodontic instrument, particularly an instrument for drilling a root canal in a patient's tooth, the instrument having a longitudinal axis and comprising a working area for forming and/or shaping and/or cutting and/or cleaning the wall of the root canal of the tooth, the working area being equipped with a supporting end piece that can be attached to a mounting.

BACKGROUND OF THE INVENTION

Cleaning and preparing root canals of a tooth for receiving filling material is accomplished using drilling instruments with an active portion called the working portion, the purpose of which is to shape and clean the root canal in preparation for receiving the materials used to treat and fill it.

Root canals often have specific shapes with complex curves and narrow cross-sections formed of constricted or oval areas that do not lend themselves to the introduction of preliminary shaping instruments. This is why instruments known as files must have characteristics that sometimes are contradictory: the files must be fine but resistant, yet flexible enough to conform to the curves of the root canal and reach the end of the canal, while nevertheless remaining durable enough to shape and cut the walls of the canal.

These exigencies oblige the odontologist to undertake a preparatory root canal treatment process using a broad array of tools and working progressively to adapt to the root canal morphology, the array of tools having various structures and dimensions. The intervention begins with a flexible fine instrument which will then be replaced by instruments of increasing cross-section until the root canal has an interior cavity large enough to receive the filling material. This is a long, delicate series of operations, being mindful that for safety reasons, the treating and filling material must completely fill the root canal and taking precautions to ensure that no residual air remains at the base of the cavity created in order to prevent any growth of bacteria and eventual infection.

These instruments are difficult to introduce into the root canal. In addition, to date there is no universal instrument adapted to the morphology of the root canal to be treated which would perform all the preparatory operations in one procedure. There is a risk of instruments cracking, becoming blocked in the canal, or greatly over-heating, which may cause breakage. This risk is notoriously present when using mechanically driven instruments made of nickel-titanium alloy, which wear out and must be carefully monitored by the odontologist throughout use. There is no doubt that using several different instruments in succession increases not only the cost of the intervention, but the complexity of the odontologist's work and risk to the patient.

U.S. Publication No. US2010/0233648 describes a method and an endodontic instrument made of superelastic material. A rod of superelastic material is set into a shaped configuration to form an instrument, such that the instrument may be inserted into a root canal in a configuration different than the shaped configuration and revert towards its shaped configuration during the endodontic procedure. In order to form the rod into a desired instrument shape, the rod is compressed (preferably ranging from about 550 MPa to about 1500 MPa) between heated forming surfaces (typically between about 100° C. to about 200° C.) which cause a stress on the rod.

When the instrument is made of a flexible metal alloy, the instrument is designed to resume its retracted shape through a mechanical action after it has been used in the expanded structured shape.

A significant drawback to conventional root canal procedures is that a practitioner must generally use a series of endodontic files to clean out and shape a diseased root canal. Typically, this series of instruments consists of a set of files of increasingly larger diameter and, as a result, an increasing taper, as the length of the working portion is often maintained substantially constant. Sets of such files are used to sequentially and gradually enlarge the root canal until the desired shape is achieved. A stepped enlargement in relatively small increments is believed to be an important part of the conventional strategy of avoiding undesirable damage to and other effects on the tooth structure during the enlargement process, and in avoiding imposition of too much torsional load or stress on the material comprising the instrument. In this regard, a set of instruments are often used only once for a particular patient and then discarded, with each instrument in the set provided at substantial individual expense. Accordingly, there is a need for an improved endodontic file design that limits the number of endodontic files necessary to achieve a desired bore shape or degree of enlargement during root canal therapy/filing procedures.

BRIEF DESCRIPTION OF THE DRAWINGS

The present invention and its principal advantages will be more apparent from the description of various embodiments, with reference to the attached drawings, in which:

FIGS. 3A and 3C represent another variation of an expandable instrument according to the invention in a first operating state in the root of a tooth, with FIG. 3C representing a cut into the root along axis 3C-3C;

FIG. 8A is an enlarged diagrammatic view of the ground nitinol wire of FIG. 8, following affixing of a conventional drive coupling to the shank thereof, while

FIG. 13 diagrammatically shows opening of the two part mold, following rapid cooling thereof, for removing the dental tool or instrument with the memorized shape;

FIG. 14 diagrammatically shows the dental tool or instrument with the memorized shape;

FIG. 14A diagrammatically shows straightening of the dental tool or instrument of FIG. 14, following cooling thereof to a temperature below its transition temperature;

FIG. 14B diagrammatically shows partial removal of the straightened dental tool or instrument of FIG. 14, following suitable cooling thereof into its martensitic phase;

DETAILED DESCRIPTION OF THE EMBODIMENT

Figure 1A:
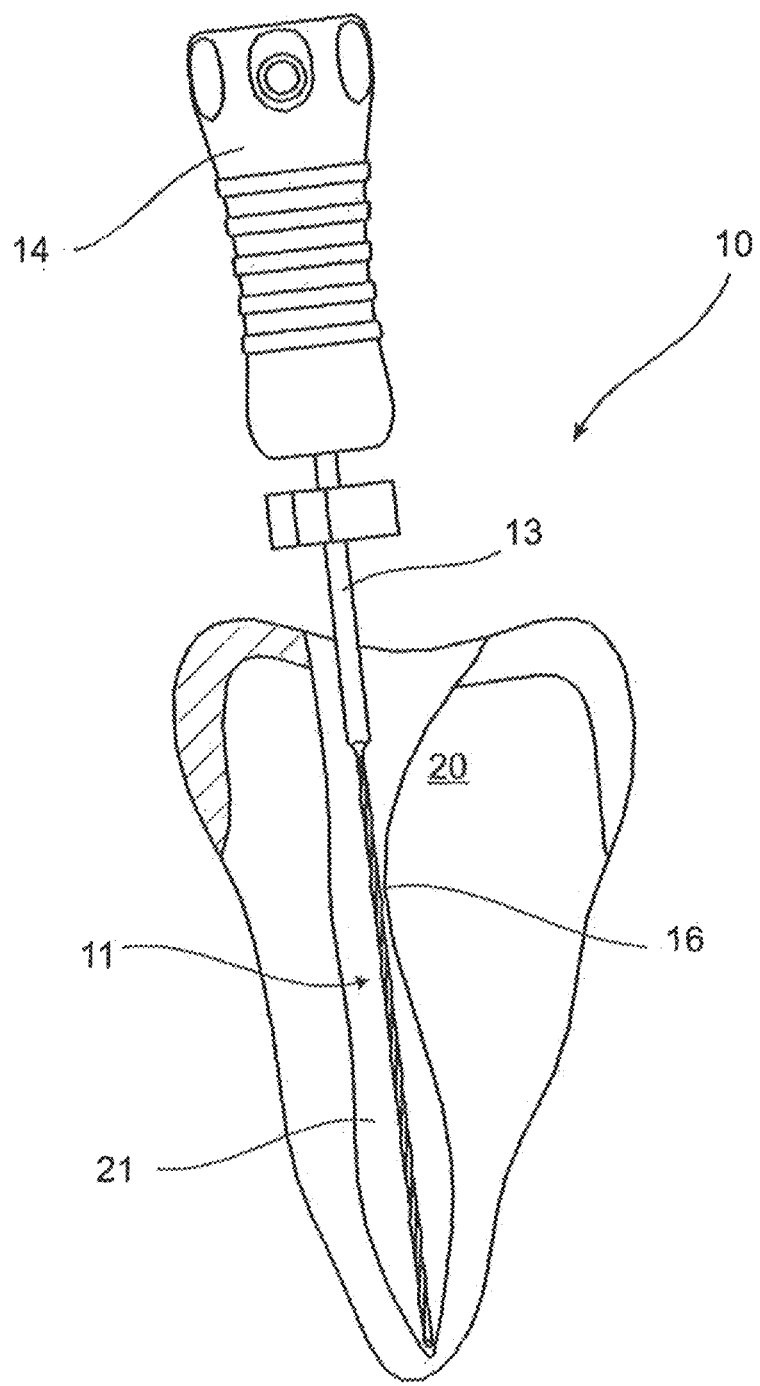
FIG. 1A represents an instrument according to the invention in the shape of a flat auger at the time of its introduction into the root canal of a tooth.

The instrument represented by FIGS. 1A through 1D is a manual type of instrument designed to be affixed to the extremity of a handle allowing the practitioner to scrape the inwardly facing surface of the generally oval root canal of a patient's tooth essentially using back and forth movements and pivoting movements around the instrument's longitudinal axis A. The instrument 10 comprises a working area 11 made of metal wire comprising one or more strands extending into a supporting end piece 13 held by a mounting14, in this case a handle allowing the practitioner to manipulate the instrument. FIG. 1A represents instrument 10 in the position of introduction into root canal 21 of a tooth 20. In this position, working area 11 of instrument 10 is in what is called the retracted position, in this case, generally rectilinear, which facilitates its introduction into root canal 21 and lets it pass easily through narrowing 16 visible in the canal. At ambient temperature, working area 11 maintains its retracted generally rectilinear configuration because of the metal alloy it is made of that has a property known as "shape memory." This quality, known in itself, permits a suitable metal alloy to have a first geometric shape in a given range of temperatures and to assume a different geometric shape after passing to another temperature. In this case, working area 11 of the instrument, made of nickel-titanium based alloy, is generally rectilinear at ambient temperature, for example from 0 to 35° C., preferably between 10 and 30° C. and especially of the order of 20° C., and it assumes an expanded structured configuration at a higher temperature. At "low" temperature the material is in a phase called "martensitic" and its shape is relatively flexible and malleable which facilitates introduction of the instrument into the root canal. At a higher temperature, the material enters a phase known as "austenitic" and the instrument assumes a structured configuration allowing it to shape the canal walls, regardless of the canal's shape. To bring the material from its martensitic phase to its austenitic phase, depending upon the materials, a first temperature variation is applied, such as an elevation, located within a range of temperatures from 0° to 60° C. and preferably from 25° to 40° C. To return the material from its austenitic to its martensitic phase, depending upon the materials, a second temperature variation is applied, such as lowering the temperature to a value called the transformation value, situated within a range of temperatures extending from 60° to 0° C. and preferably 40° C. and 25° C. for certain nickel alloys.

Alloys that are useful for their memory properties are principally copper-zinc-aluminum-nickel, copper-aluminum-nickel and zinc-copper-gold-iron alloys. Obviously other alloys with similar properties could be used.

The temperature increase can be accelerated using heating means incorporated in the instrument base or using exterior means such as, for example, sodium hypochlorite (NaOCl) which is used to disinfect the root canal. This compound may be injected through a heating syringe currently used by practitioners in the field.

Figure 1B:
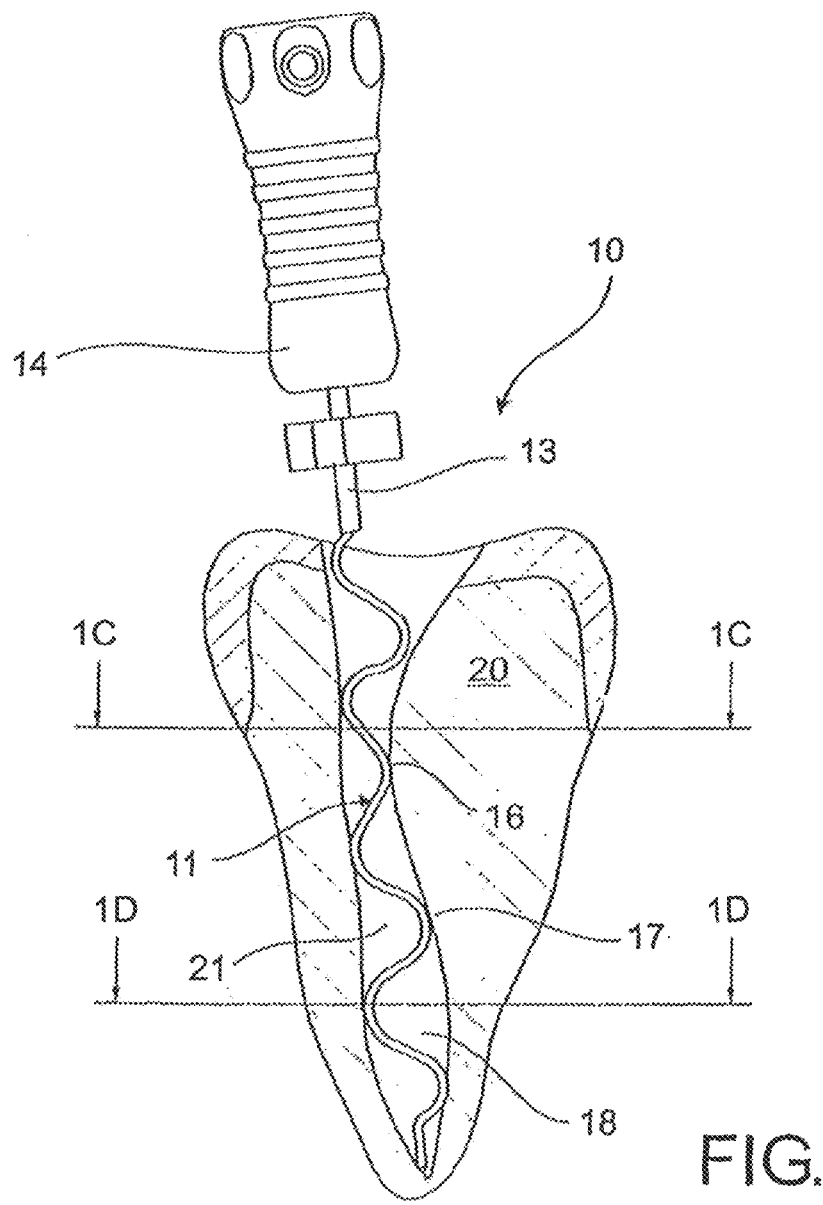
FIGS. 1B through 1D represent the instrument of FIG. 1A after introduction into the root canal of the tooth, with FIGS. 1C and 1D respectively representing cross sections of in the tooth along section lines 1C-1C and 1D-1D, respectively.
Figure 1C:
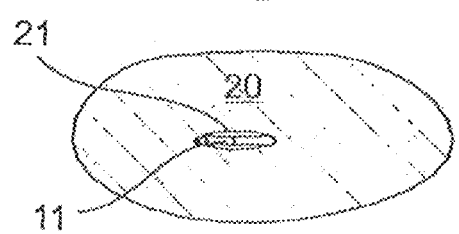
Figure 1D:
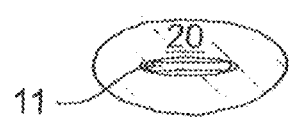

The expanded structured shape assumed by working area 11 of instrument 10 is shown in FIGS. 1B through 1D. Working area 11 in this exemplary embodiment assumes the shape of a flat auger essentially filling the entire space of root canal 21 as shown in FIGS. 1C and 1D. This auger is extremely flexible so that it adapts to the internal shape and contour of root canal 21. In narrow portion 16 of the canal, loops 17 on the auger are less pronounced than in enlarged sectors 18 and 19, corresponding to the bottom and the entry to canal 21, respectively.

Figures 2A, 2C:
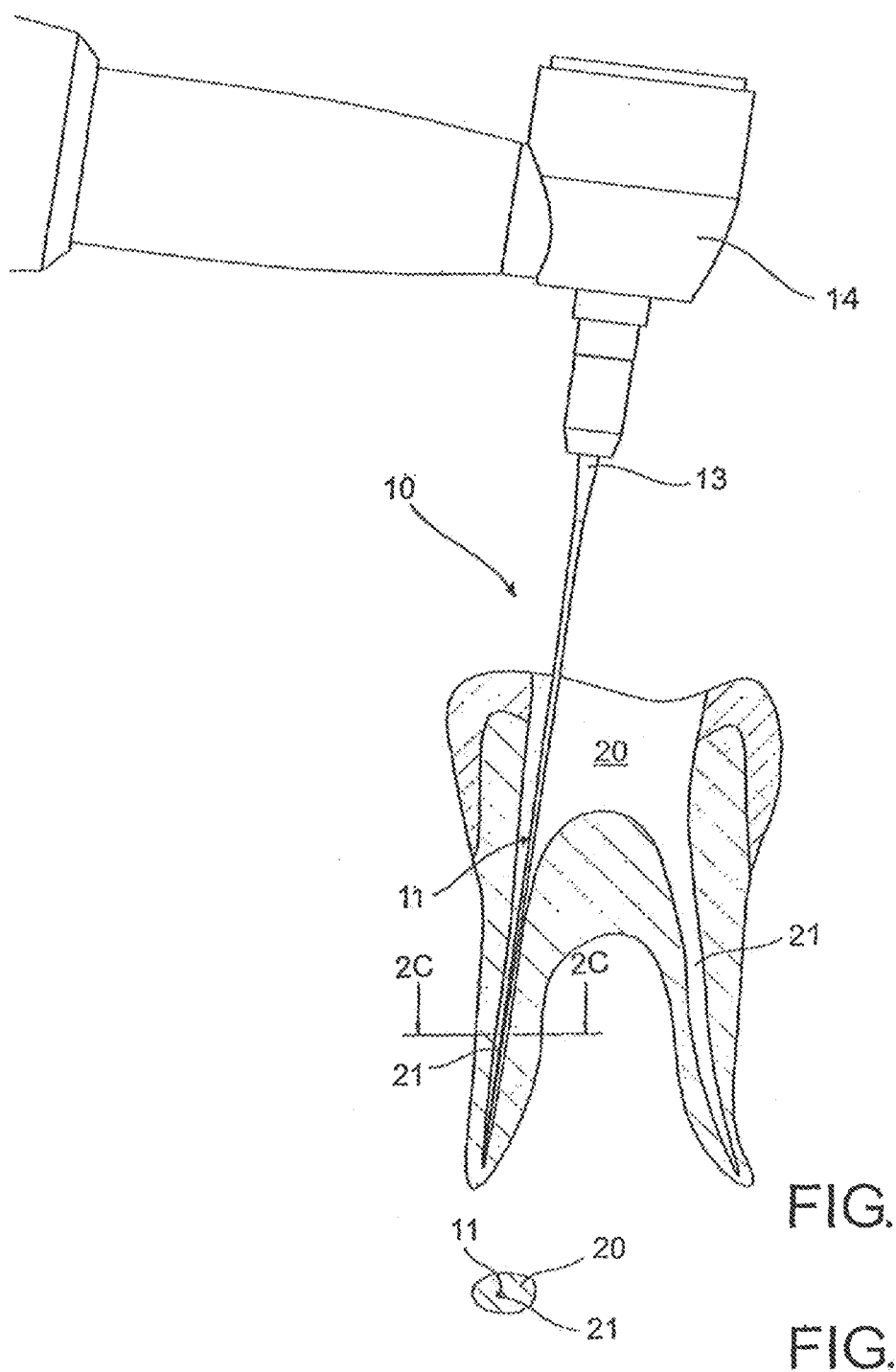
FIGS. 2A and 2C represent another type of embodiment of the instrument of the invention at the time of its introduction into the canal of the root a tooth, with FIG. 2C representing a cross section into the root of the tooth along section line 2C-2C.
Figures 2B, 2D:
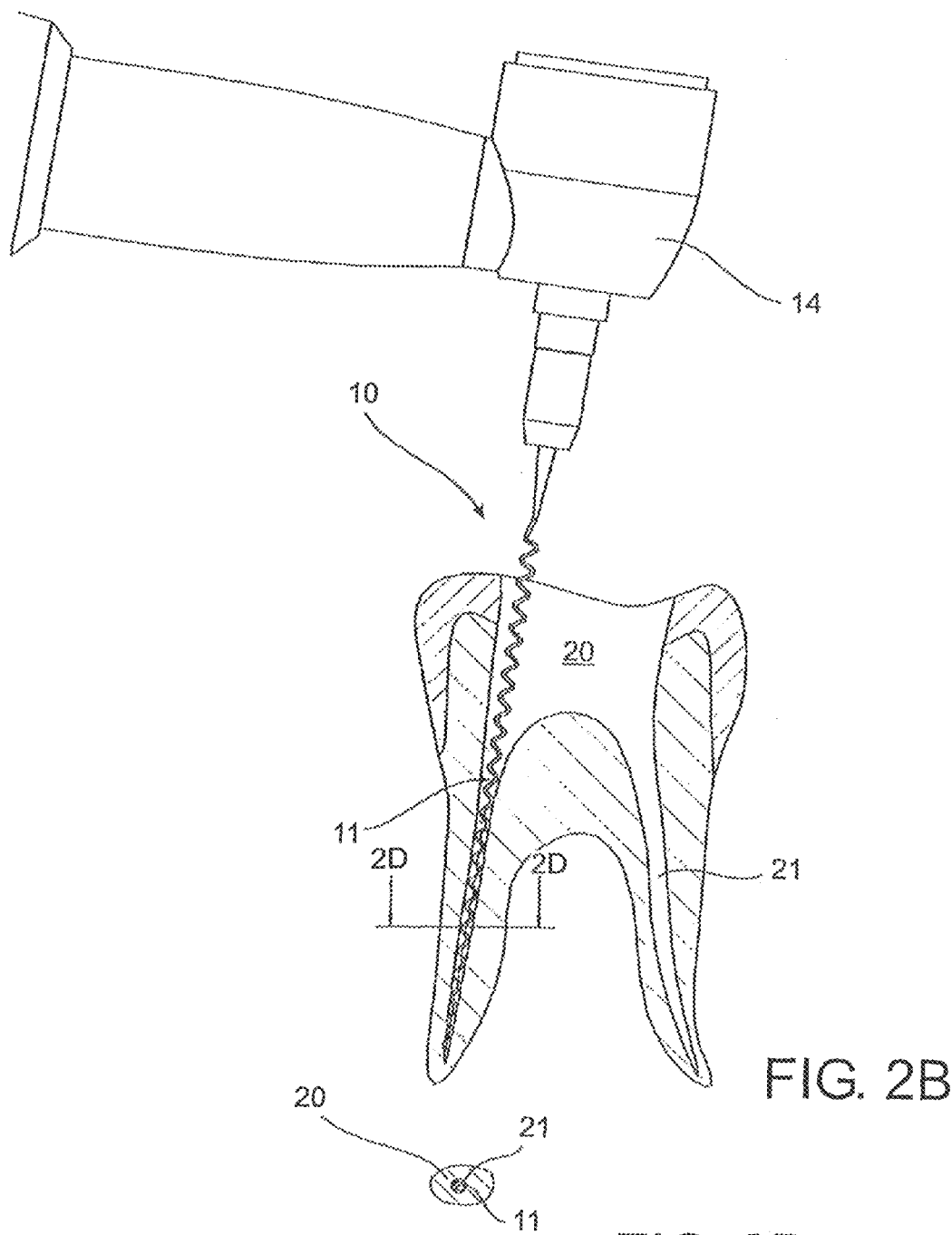
FIGS. 2B and 2D represent the instrument of FIG. 2A after introduction into the canal of the root of a tooth, with FIG. 2D representing a cross section into the root along section line 2D-2D.

FIGS. 2A through 2D represent an instrument 10 according to the invention, of the mechanically driven type, engaged in one of canals 21 of a molar type tooth 20 with two root canals. In FIGS. 2A through 2C, working area 11, in its retracted configuration, is generally rectilinear, allowing easy introduction into root canal 21. In FIGS. 2B and 2D, working area 11 has assumed its expanded structured configuration following a temperature increase resulting either from contact with the patient's body or from a heating resistor (not shown) present in mounting 14 that supports instrument 10. In the example shown, the instrument is mechanically rotated and when in its structured state, it is shaped like a corkscrew. Working area 11 on instrument 10 is also of sufficiently flexible consistency that its cross-section can adapt to the cross-section of root canal 21, which is more or less conical. For this reason working area 11 is made with a metal alloy wire with shape memory that assumes its expanded structured configuration following a temperature elevation or a temperature change. The wire may be generally circular or perhaps angular in cross-section such that the instrument functions as either a smoothing, cutting, or abrasive tool according to the result desired. The practitioner may use several instruments with different or complementary functions depending on the initial shape of the root canal to be treated.

Figure 3B:
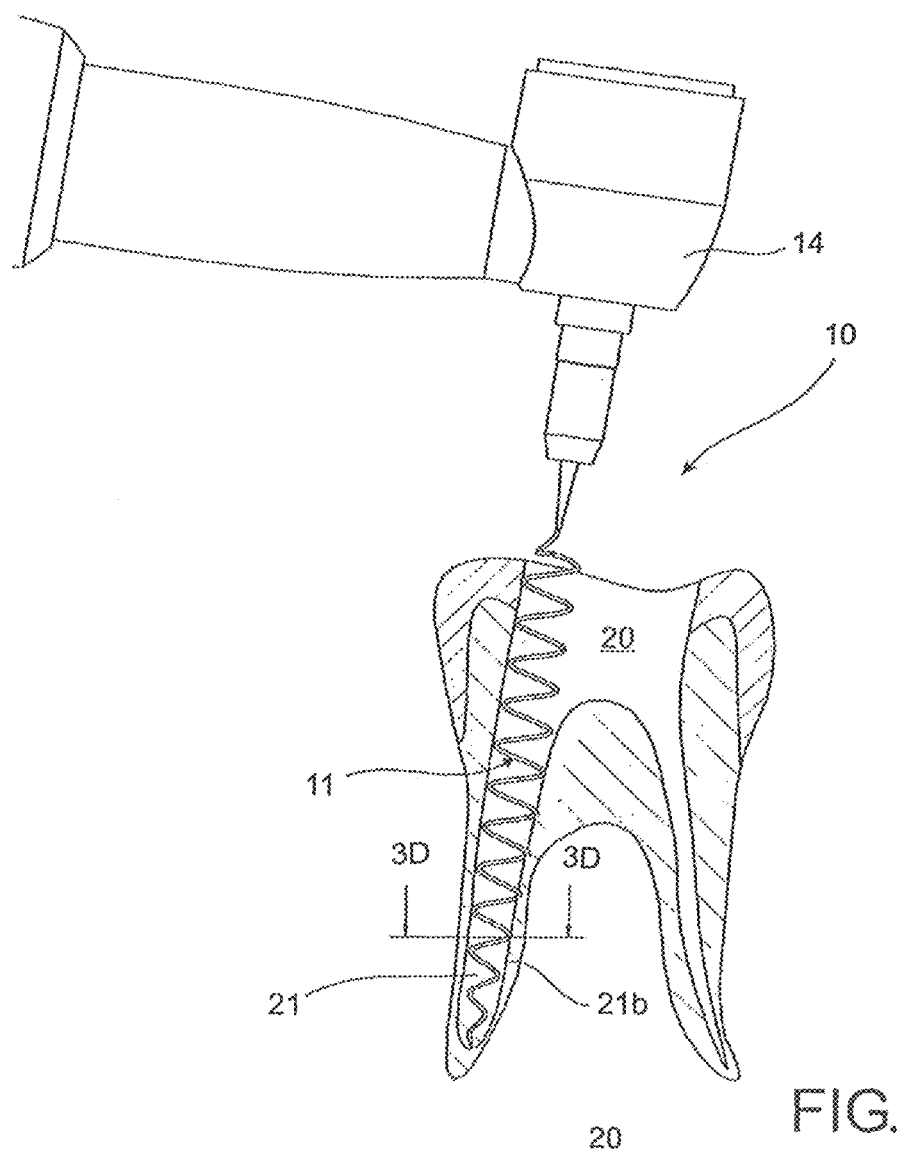
FIGS. 3B and 3D represent the instrument called the expandable instrument in FIG. 3A in a second operating state, with FIG. 3D representing a cut into the treated root of the tooth along axis 3D-3D.
Figure 3D:
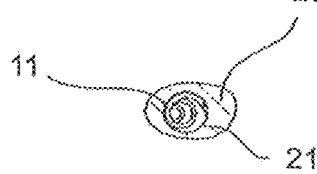

FIGS. 3A through 3D represent another embodiment of an instrument according to the invention of the mechanically driven type. This instrument 10, called an expandable instrument, has specific characteristics allowing it to adapt to the shape and dimensions of a root canal or "machine" the canal to give it the shape and dimensions desired for the subsequent root canal treatment. Instrument 10, in the state represented in FIGS. 3A and 3C, is introduced into one of the root canals 21 in tooth 20. This canal comprises a slight bulge 21a in its central portion, followed by a narrowing 21b. Working area 11 on instrument 10 adapts to this configuration. Like the instrument illustrated in FIGS. 2A through 2D, this instrument is mechanically rotated by its mounting 14 and depending upon the cross-section of the metal wire constituting it, its action produces either machining, cutting, abrasion or smoothing of the walls of root canal 21. In the present case, the goal is to enlarge the upper portion of the canal while eliminating narrowed portion 21b in order to facilitate introduction of the filling substance. To do this, instrument 10 dilates, assumes the shape of a corkscrew with a generally circular cross-section, and acts on the walls by cutting or eroding the material of the tooth body, as shown in FIGS. 3B and 3D.

Figure 4A:
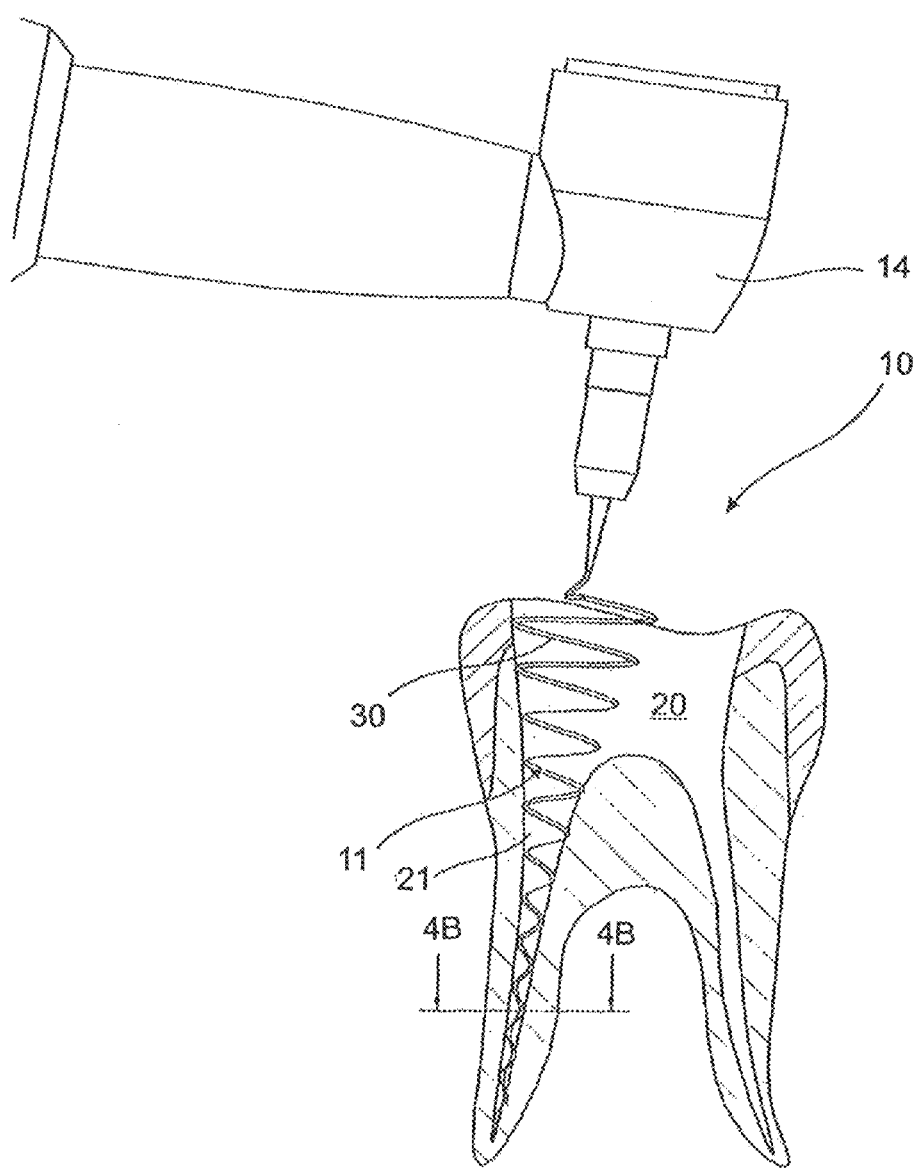
FIGS. 4A and 4B represent an expandable instrument similar to that in FIGS. 3A through 3D in a different working configuration in the root of a tooth, with FIG. 4B representing a cut into the root along axis 4B-4B.
Figure 4B:
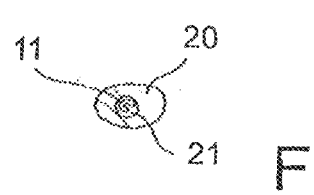

In the embodiment shown in FIGS. 4A and 4B, expansion of instrument 10 occurs essentially in upper portion 30 of working area 11 and the objective is to shape root canal 21 into a cone. Working area 11 may be a cutting, abrasive or smoothing one depending on what shape is contemplated for canal 21.

Figures 5A, 5B:
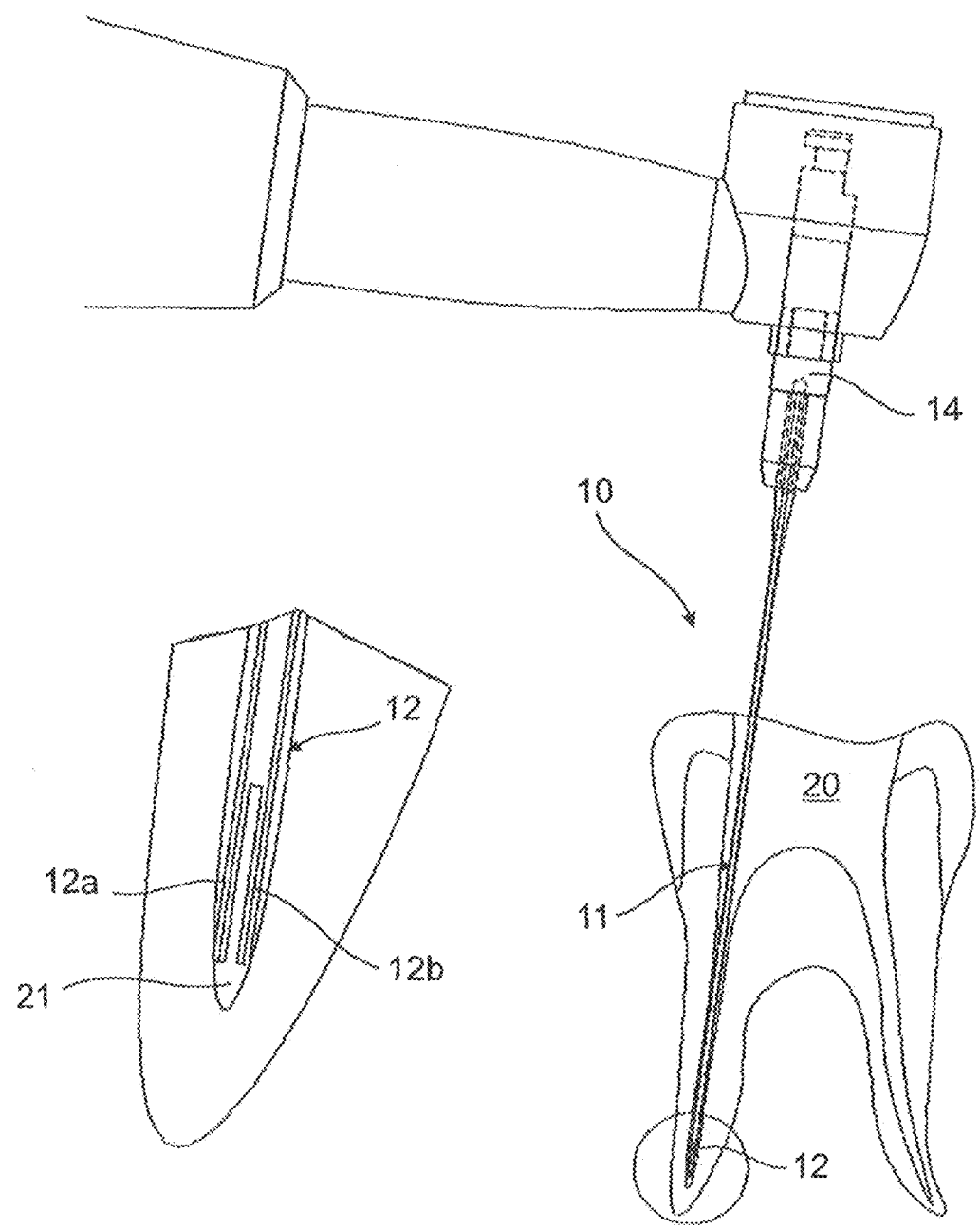
FIG. 5A illustrates a variation of the instrument of the invention called a tubular instrument introduced into the root of a tooth but in the inoperative position.
FIG. 5B is an enlarged view of the extremity of the working area of the instrument of FIG. 5A in inoperative position.
Figures 6A, 6B:
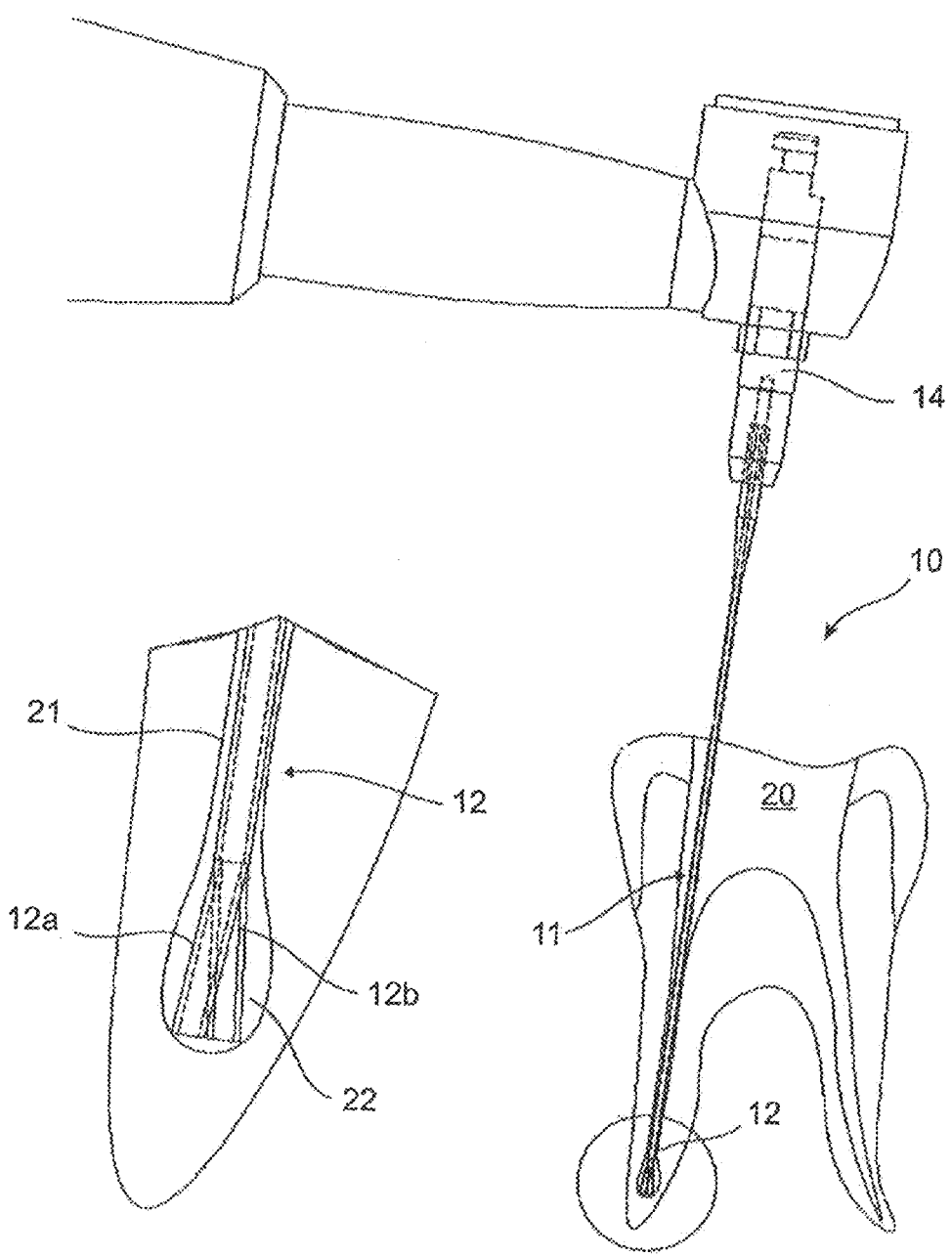
FIG. 6A illustrates the instrument of FIGS. 5A and 5B in the operative position inside the root of the tooth.
FIG. 6B is an enlarged view of the extremity of the working area of the instrument of FIG. 5A in the operative position.

FIGS. 5A and 5B illustrate another embodiment of instrument 10 in which working area 11 is generally tubular and has a twisted appearance. Lower extremity 12 of this working area 11 is split axially for a certain length and comprises two sectors 12a and 12b that are visible in FIG. 5B. When the working area (whose extremity 12 is enlarged in FIG. 5B) is in the inoperative position, the two sectors 12a and 12b are juxtaposed in the axial extension of the rest of working area 11. Introducing the working area of instrument 10 into root canal 21 is easy because of its tubular rectilinear configuration. In its working position shown in FIGS. 6A and 6B, lower extremity 12 has opened following a temperature elevation by virtue of the shape memory properties of the alloy forming the instrument 10, and the two sectors 12a and 12b form an angle between them that describes a more or less open cone when the tool is rotated by its turning mounting 14. The odontologist's objective is to create an enlarged cavity 22 at the extremity of root canal 21, the cavity being destined to receive the filler paste and prevent entrapment of air microbubbles at the canal base. Air microbubbles actually contain oxygen which can feed bacteria and decay, producing a more or less long term infection.

Turning now to FIGS. 7-21B, a further embodiment of the present invention will now be described. As this embodiment is very similar to the previously discussed embodiments, only the differences between this new embodiment and the previous embodiment will be discussed in detail while identical elements will be given identical reference numerals.

Figure 7:
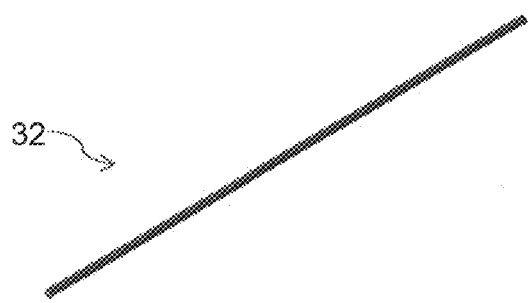
FIG. 7 is a diagrammatic view of a nitinol wire for use in manufacturing a dental tool or instrument according to the present invention.

According to this embodiment, the dental tool or instrument 10, according to the present invention, is manufactured from a nitinol wire 32 (e.g., typically about 56% nickel and about 44% titanium by weight). This nitinol wire 32 is in an austenitic phase at room temperature (about 72 degrees Fahrenheit or about 22 degrees Celsius) in order to be able to machine the nitinol wire 32 into the desired dental tool or instrument, see FIG. 7. That is, when the nitinol wire 32 is at a temperature below the transition temperature, the Nitirol wire is in its martensitic phase in which the nitinol wire 32 is normally pliable, malleable and/or temporarily deformable into a desired shape, e.g., can be manipulated into a desired bent configuration or shape or into some other desired configuration or shape. However, once the nitinol wire 32 reaches a temperature at or above the transition temperature, e.g., typically well below room temperature in this instance, the nitinol wire 32 naturally and automatically transitions back into its austenitic phase where the nitinol wire 32 becomes more rigid and naturally returns back to its initially manufactured configuration or shape, which is typically a linear configuration or shape, as generally shown in FIG. 7. In the austenitic phase of the nitinol wire 32, the nitinol wire 32 always adopts its manufactured linear configuration or shape which is particularly well suited and beneficial for machining/grinding/converting the nitinol wire 32 into a dental tool or instrument 10, as is conventional in the art.

According to the present invention, the dental tool or instrument 10 is first manufactured by selecting a suitable nitinol wire 32 for manufacture of the dental tool or instrument 10. Since the dental tool or instrument 10 will be utilized in the mouth of a patient, it is desirable for a final transition temperature of the nitinol wire 32, and the resulting dental tool or instrument 10, to be slightly below body temperature, i.e., about 90.5±4 degrees Fahrenheit (i.e., 32.5±3 degrees Celsius). However, it is to be appreciated that for other applications, a nitinol wire 32 having a different transition temperature, e.g., either higher or lower than about 90.5±4 degrees Fahrenheit (i.e., 32.5±3 degrees Celsius), may be utilized without departing from the spirit and scope of the present invention.

As is conventional in the art, the selected nitinol wire 32, which is manufactured in a conventional manner, normally has conventional super elastic properties. That is, the nitinol wire 32 has both a martensitic phase, in which the nitinol wire 32 is generally malleable or temporarily deformable into a desire configuration or shape as long as the nitinol wire 32 remains at a temperature below its initial transition temperature of the nitinol wire 32, as well as an austenitic phase, in which the nitinol wire 32 will automatically return back to its originally manufactured configuration or shape, e.g., which is typically its originally manufactured linear configuration or shape, as soon as the temperature of the nitinol wire 32 reaches or exceeds the initial transition temperature of the nitinol wire 32.

According to the present invention, as discussed below in further detail, the resulting dental tool or instrument 10 will have a final transition temperature of slightly below body temperature, i.e., about 90.5±4 degrees Fahrenheit (i.e., 32.5±3 degrees Celsius). However, during the manufacturing process of the nitinol wire 32 processing, it is desirable for the nitinol wire 32 to have an initial transition temperature which is typically well below room temperature. This ensures that the nitinol wire 32 is in an austenitic phase, i.e., relatively firm at room temperature, which assists with machining/grinding/converting the nitinol wire 32, at room temperature, into a dental tool or instrument 10.

Figure 8:
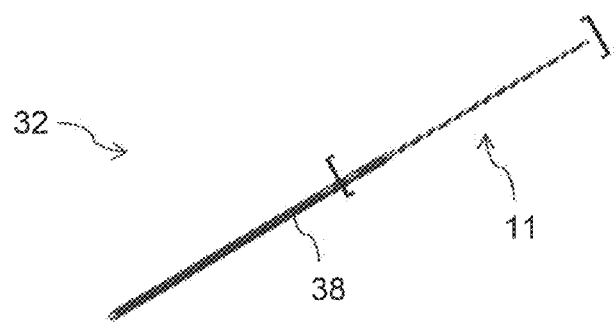
FIG. 8 is a diagrammatic view of ground first portion of the nitinol wire which forms a working area of the dental tool or instrument.

After selecting a suitable nitinol wire 32 for manufacturing the dental tool or instrument 10, the nitinol wire 32 in then subjected to a grinding or cutting operation (FIGS. 8 and 8A) in which at least one, and possibly two or more longitudinal or elongate cutting surfaces or edges 34, e.g., helical cutting surfaces or edges, are cut or otherwise formed along a longitudinal length or axis A of only a first portion of the nitinol wire 32, e.g., typically in a helical shape. Such ground first portion of the nitinol wire 32 generally forms a working area 11 of the dental tool or instrument 10, as generally shown in FIG. 8. A second opposed end portion of the nitinol wire 32 remains substantially unground or unaltered and thereby forms a shank 38 of the dental tool or instrument 10. The opposite, unground end of the dental tool or instrument 10 forms a shank 38 which assist with assists with coupling the dental tool or instrument 10, during use.

Figure 8A:
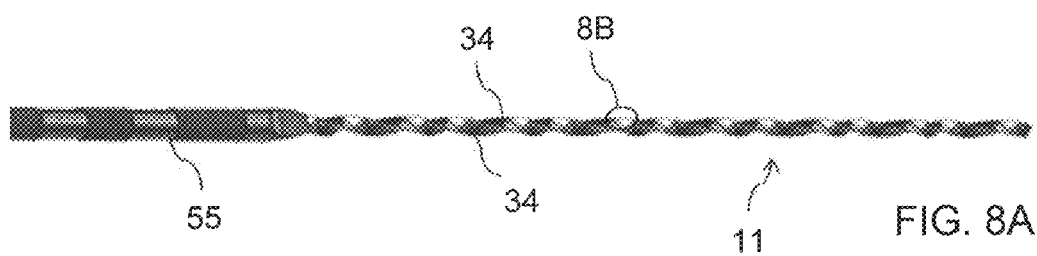

Following completion of the grinding process, the dental tool or instrument 10 is then cut to a desired length. Thereafter, as shown in FIG. 8A, a conventional drive coupling 55, which facilitates coupling and grasping of the dental tool or instrument 10 by a conventional rotary tool 59, is affixed, in a conventional manner, to the shank 38 of the dental tool or instrument 10.

It is important to note that formation of the working area 11 is formed purely by a grinding, cutting or other similar machining operation. In the past, helical cutting surfaces have been introduced to the wire 32 by applying twisting motions under certain conditions, e.g., applying extreme pressures and low temperatures. However, such twisting motions introduced unwanted stress and tend to cause undesirable fatigue in the nitinol wire 32 and is thus to be avoided. It is to be appreciated that stress and fatigue tend to lead to the dental tool or instrument 10 breaking after a limited amount of rotation and/or bending. That is, breakage tends to occur after only a nominal load is repeatedly applied and then removed, even when the maximum cyclic stress level applied was much lower than the ultimate tensile strength, and in fact, much lower than the yield stresses of either the martensitic or the austenitic phases of the instrument or tool 10. For this reason, the prior art wires tend to break or fracture prematurely and thus are generally suitable for only a single application.

Figure 8B:
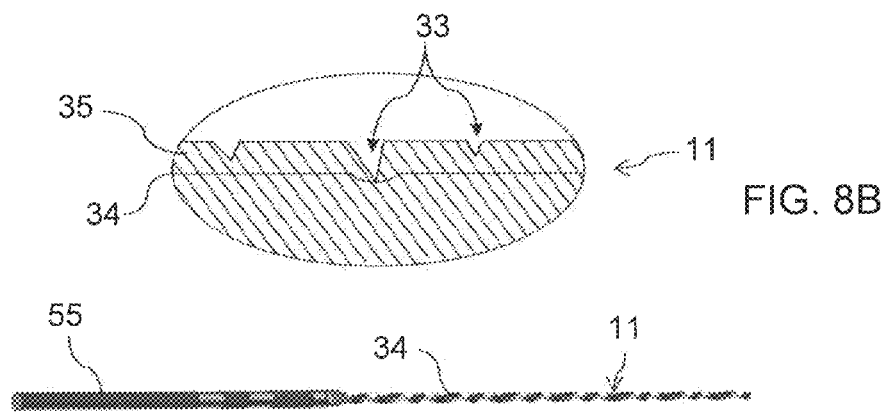
FIG. 8B is an enlarged diagrammatic partial section view of area 8B of FIG. 8A.
Figure 9:
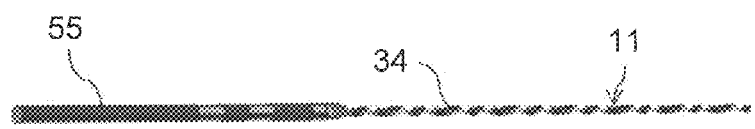
FIG. 9 is a diagrammatic view of a washed and electropolished the dental tool or instrument according to the present invention.
Figure 10:
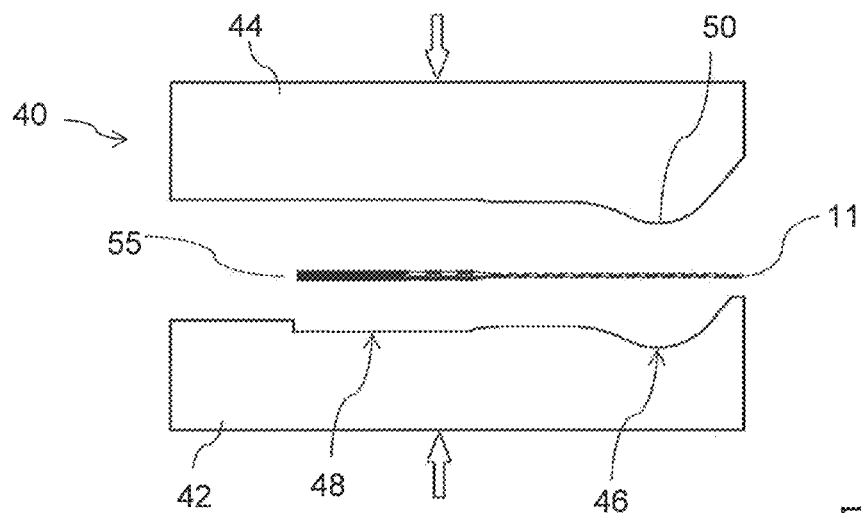
FIG. 10 diagrammatically shows a two part mold for molding a desired memorized shape into the dental tool or instrument.

Following formation of the at least one, and possibly two or more longitudinal or elongate cutting surfaces or edges 34 along the working area 11 of the dental tool or instrument 10 and affixing the drive coupling 55, the dental tool or instrument 10 is then subject to a washing and an electropolishing process. During this washing and an electropolishing process, a very thin layer or portion 35, e.g., possibly 0.01-0.03 mm (see FIG. 8B), of the exterior surface of the dental tool or instrument 10 is removed therefrom. Such removal of a very thin layer or portion 35 of the exterior surface of the dental tool or instrument 10, by the electropolishing process, tends to remove or, at the very least, smooth out the contour of any very small cracks or other imperfections or deformities 33, which may possibly have been formed in the exterior surface of the dental tool or instrument 10 during the grinding process, and such electropolishing process renders the dental tool or instrument 10 more resistant to breakage and/or fatigue during use.

As a result of the above process, the dental tool or instrument 10 is designed so that the dental tool or instrument 10 can be rotated at a rotational speed of about 900±100 rpms, while performing a root canal procedure, for a duration of time of at least a few minutes or so, without fracturing and/or breaking thereby extending and prolonging the useful life of the dental tool or instrument 10 and minimizing the possibility that the dental tool or instrument 10 will inadvertently break or fracture, during use thereof, possibly leaving a broken or a fractured portion of the dental tool or instrument 10 in the root canal.

After the washing and electropolishing process and cutting to a desired dental tool or instrument 10 length, the dental tool or instrument 10 is then ready to have both: a) its initial transition temperature altered to its final transition temperature so that the transition temperature of the dental tool or instrument 10 will be about or slightly below body temperature, and b) heat molded to memorize a desired shape or configuration which has at least one bend, undulation, curvature, discontinuity, bulge or protrusion 36 formed within and along the working area 11 of the dental tool or instrument 10. As shown in FIG. 14, the at least one protrusion 36 is formed only along a portion of the working area 11, normally located at or adjacent the free tip of the dental tool or instrument 10 and spaced and remote from the shank 38. Typically, the at least one protrusion 36 is formed closer the free tip of the dental tool or instrument 10 than to the shank 38 of the dental tool or instrument 10. The at least one protrusion 36 and the shank 38 of the dental tool or instrument 10 both define and lie in a single plane. In addition, preferably the dental tool or instrument 10 is not twisted when being placed within the mold 42 so as to minimize stress induced into the dental tool or instrument 10.

The at least one protrusion 36 generally has a curved or an arcuate shape having a length L of between about 1 and 16 mm (measured along a longitudinal axis A of the dental tool or instrument 10) and a width W (measured with respect to the longitudinal axis A of the dental tool or instrument 10) of between about 0.1 to about 3.0 mm or so. It is to be appreciated that the overall shape of the at least one protrusion 36 to be memorized by the working area 11 of the dental tool or instrument 10 can vary, depending upon the particular application, without departing from the spirit and scope of the present invention. The important aspect of the at least one protrusion 36 is that, upon rotation of the dental tool or instrument 10, the at least one protrusion 36 increases the radius and/or volume circumscribed by the dental tool or instrument 10 as the dental tool or instrument 10 rotates. This increased radius and/or volume, of the dental tool or instrument 10, facilitates a more complete scraping and removal of pulp from the inwardly facing surfaces of a root canal, especially for the complex curved and narrowed sections of the root canal which normally do not lend themselves to complete removal of the pulp. In addition, according to the present invention, if desired two or more sequential protrusions 36 may be formed within the working area, one sequentially after the other (not shown), depending upon the particular application.

As noted above, it is highly desirable for the dental tool or instrument 10 to be in its austenite phase, at room temperature, during the manufacturing process. That is, as long as the dental tool or instrument 10 is at a temperature above its initial transition temperature, e.g., typically a temperature of about 50±10 degrees Fahrenheit (10±5 degrees Centigrade) in this instance, the dental tool or instrument 10 is not malleable or temporarily deformable. As such, the working area 11 of the dental tool or instrument 10 does not readily conform or mold into a desired shape, i.e., the shape of the desired at least one protrusion 36.

The initial transition temperature of the dental tool or instrument 10 is altered, according to the present invention, by placing the dental tool or instrument 10 in a mold 40 and applying only minimal pressure, e.g., the weight of a top mold, heating the dental tool or instrument 10 to a desired temperature for a desired duration of time. As generally shown in the FIG. 10, the base mold 42 has a cavity 46 formed therein which includes a negative impression 48 of the at least one protrusion 36. Each cavity 46 of the mold 40 is sized and shaped to receive and accommodate a dental tool or instrument 10 therein and mold the working area 11 of the dental tool or instrument 10 into the desired at least one protrusion 36. When the dental tool or instrument 10 is initially placed within the cavity 46 of the base mold 42, the working area 11 of the dental tool or instrument 10, since the dental tool or instrument 10 is still currently in its austenitic phase, does not follow or conform to the contour of the negative impression 48 which is formed in the base mold 42 and is the desired shape to be obtained in the final end product of the dental tool or instrument 10.

In order to force the dental tool or instrument 10, still in its austenitic phase, to closely follow and conform to the contour of the at least one protrusion 36 formed in the base mold 42, a mating top mold 44 engages with the base mold 42 so as to captively accommodate the dental tool or instrument 10 within the cavity 46 of the mold 40. As noted above, the top mold 44 has a mating positive impression 50 which corresponds to the negative impression 48 of the at least one protrusion 36 to be formed in the working area 11 of the dental tool or instrument 10. Accordingly, as the top mold 44, with the positive impression 50 of the at least one protrusion 36, mates with the base mold 42, the working area 11 of the dental tool or instrument 10 is forced or induced to adopt, conform and closely follow the contour of the mating negative and positive impressions 48, 50 of the base mold 42, which is the desired configuration or shape to be obtained and memorized by the final end product of the dental tool or instrument 10, as generally shown in FIG. 14. It is to be appreciated that the top mold 44 only applies minimal pressure, e.g., typically significantly less than a thousand pounds per square inch, more preferably less than one hundred pounds per square inch, and most preferably less than ten pounds per square inch or so, so as to completely avoid any compression of the dental tool or instrument 10. That is, the negative impression 48 and the mating positive impression 50 of the at least one protrusion 36 have a shape, size and/or diameter at least as large as the outer shape, size and/or diameter of the working area of the dental tool or instrument 10 (preferably with so clearance) so that the present invention merely reconfigures the dental tool or instrument 10 into a new desired shape of the dental tool or instrument 10 to be memorized but does not physical alter size/diameter of the dental tool or instrument 10. Typically the minimal force required to reconfigure or realign the dental tool or instrument 10 into a new desired shape to be memorized, and thereafter be heated in the mold 40, is less than a hundred pounds per square inch, more preferably less than ten pounds per square inch, and most preferably less than a few pounds per square inch. Such minimal force on the working area 11 occurs without causing any permanent deformation (i.e., any deformation which is not reversible solely by a change in temperature) of the dental tool or instrument 10. This minimal force merely facilitates reconfiguring or realigning and maintains the dental tool or instrument 10 into a new memorized shape so that, following the above discussed heating and cooling process, the dental tool or instrument 10 will memorize this new shape in which the newly memorized superelastic configuration of the dental tool or instrument 10 has a linear shank 38 and a non linear working area 11, as generally shown in FIG. 14.

Figure 11:
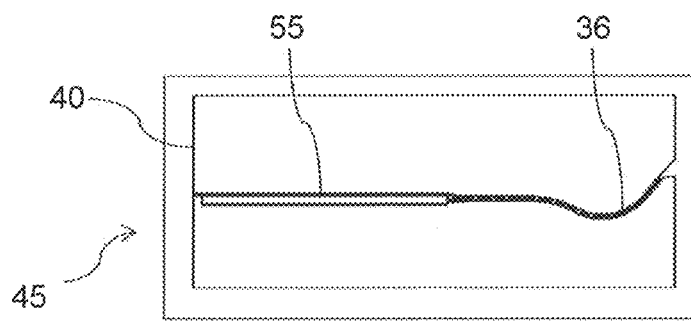
FIG. 11 diagrammatically shows a two part mold, in its closed position, conforming the dental tool or instrument into the desired shape to be memorized and heated in an oven.

When mating the top and base molds 44, 42 with one another, only a minimal amount of force or pressure is required and this minimizes possible metal fatigue. Moreover, no compression of the dental tool or instrument 10 occurs. Thereafter, the mold 40, with the one or more accommodated dental tool(s) or instrument(s) 10 accommodated therein, is then heated to a desired temperature by a conventional heater 45. The heat supplied to the dental tool or instrument 10 is designed to both: a) alter the initial transition temperature of the resulting dental tool or instrument 10 to a final transition temperature, and b) permanently "memorize" the molded shape of at least one protrusion 36 formed in the mold 40, as generally shown in FIG. 11, for example.

As a result of this process, once the dental tool or instrument 10 is heated for a sufficient duration of time in the mold 40 and then subsequently cooled, as described below in further detail, the dental tool or instrument 10 memorizes the shape of the mating negative and positive impressions 48, 50 of the at least one protrusion 36 formed in the mold 40. In addition, due to this heating process for a sufficient duration of time in the mold 40, the initial transition temperature of the dental tool or instrument 10 is altered from its initial transition temperature of about 50±10 degrees Fahrenheit (10±5 degrees Centigrade) to its final transition temperature of slightly below body temperature, i.e., about 90.5±4 degrees Fahrenheit (i.e., 32.5±3 degrees Celsius). As a result, thereafter each and every time that the temperature of the dental tool or instrument 10 is at or above the final transition temperature of the dental tool or instrument 10, i.e., any time the dental tool or instrument 10 is in its austenitic phase, the dental tool or instrument 10 will always automatically return back to this memorized molded shape of the at least one protrusion 36 which mirrors the mating negative and positive impressions 48, 50 of the mold 40.

During the heating process, the dental tool or instrument 10 is heated to a sufficient temperature which a) facilitates memorization of the molded shape of the dental tool or instrument 10, and b) also facilitates altering the initial transition temperature of the dental tool or instrument 10 to a new final transition temperature. That is, the heating temperature of the dental tool or instrument 10, which facilitates both altering the original transition temperature and memorizing the molded shape, is typically temperature of between 392 and 707 degrees Fahrenheit (200 and 375 degrees Centigrade) for a duration of time of between 30 minutes and 240 minutes. More preferably, the heating temperature of the dental tool or instrument 10, which facilitates both altering the original transition temperature to a new final transition temperature and memorizing the molded shape, is temperature of between 482 and 662 degrees Fahrenheit (250 and 350 degrees Centigrade), and most preferably, the heating temperature of the dental tool or instrument 10, to facilitate both altering the transition temperature and memorizing the molded shape, is temperature of about 572 degrees Fahrenheit (300 degrees Centigrade). More preferably, the heating time of the dental tool or instrument 10, to facilitate both altering the original transition temperature to a new final transition temperature and memorizing the molded shape, is a duration of between 45 and 90 minutes.

While the dental tool or instrument 10 is accommodated within the mold 40 and heated at the desired memorization temperature for the desired duration of time, the dental tool or instrument 10 generally anneals so as to alter it original memorized shape into a new memorized shape that the dental tool or instrument 10 will always automatically adopt and return to each and every time the dental tool or instrument 10 is at or above its new final transition temperature, i.e., when the dental tool or instrument 10 is in its austenitic phase. That is, the dental tool or instrument 10 memorizes and automatically adopts this newly memorized shape as soon as and each and every time that the dental tool or instrument 10 transitions from its martensitic phase into its austenitic phase.

Figure 12:
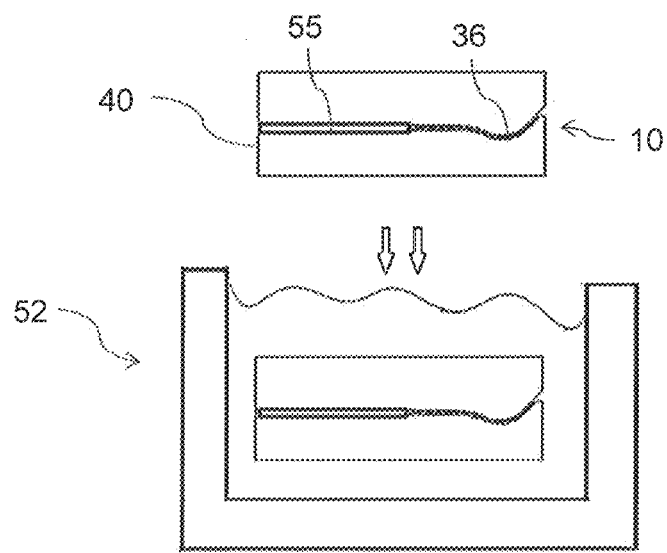
FIG. 12 diagrammatically shows a two part mold being rapidly cooled.
Figure 15:
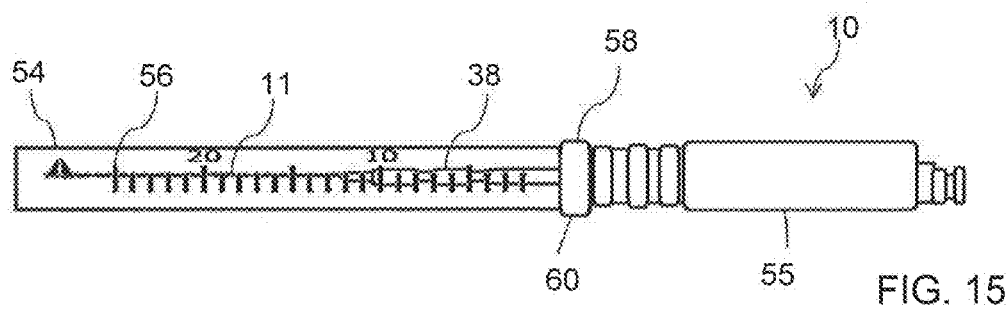
FIG. 15 diagrammatically shows the dental tool or instrument, with the memorized shape, contained within a protective case.

Following heating of the dental tool or instrument 10, within the mold 40 to the desired temperature for the desired duration of time, the mold 40 and the dental tool or instrument 10 are then both rapidly cooled, i.e., quenched in a liquid bath 52 (e.g., cold water for example), as generally shown in FIG. 12. Such rapidly cooling of the dental tool or instrument 10 assist with annealing the dental tool or instrument 10 and memorizing the shape of the at least one protrusion 36.

After quenching, the top second mold 44 is separated from the base mold 42 to open the mold 40 and permit removal of the dental tool(s) or instrument(s) 10, as generally shown in FIG. 13. As a result of the above process, a) the original transition temperature of the dental tool or instrument 10 is alter to a final transition temperature of slightly below body temperature, i.e., about 90.5±4 degrees Fahrenheit (i.e., 32.5±3 degrees Celsius), and b) the dental tool or instrument 10 memorizes its molded shape of the at least one protrusion 36 and adopts this memorized shape as soon as and each and every time that the dental tool or instrument 10 transitions from its martensitic phase into its austenitic phase. It is to be appreciated that when the dental tool or instrument 10 is at temperature below its final transition temperature, the dental tool or instrument 10 is in the martensitic phase and is bendable or pliable.

However, this memorized shape, in the form of the at least one protrusion 36, can make packaging, storage and/or transportation of the dental tool or instrument 10 somewhat difficult. In order to address this problem, following manufacture, the dental tool or instrument 10 may be sufficiently cooled by spraying the dental tool or instrument 10 with a cooling/sanitizing liquid or gas, as generally shown in FIG. 14, in order to sanitize and bring the dental tool or instrument 10 to a temperature below its final transition temperature, e.g., so that the dental tool or instrument 10 is in its martensitic phase at room temperature. Thereafter, the at least one protrusion 36, of the dental tool or instrument 10, can then be straightened manually (as generally shown in FIG. 14A) which assists insertion of the dental tool or instrument 10 into or removal from suitable packaging, such as a protective cover or case 54, as generally shown in FIG. 14B.

As noted above, in order to ensure protection of the dental tool or instrument 10, the dental tool or instrument 10, following manufacture and sterilization thereof, is packaged in the protective cover or case 54. The protection case 54 is typically a thin hollow case which closely receives and accommodates at least the working area 11 of the dental tool or instrument 10, and at least a portion of the shank 38, within an internal cylindrical compartment thereof, while the drive coupling 55 of the dental tool or instrument 10 remains located outside the protective case 54 and exposed to the external environment. That is, the drive coupling 55 remains readily accessible for engagement with a rotary tool 59 in a conventional manner. This facilitates ease of attachment of the drive coupling 55 of the dental tool or instrument 10 to the desired rotary tool 59. Lastly, the dental tool or instrument 10, accommodated within the protective case 54, is packaged within a conventional protective packaging which maintains the sterility of the dental tool or instrument 10, until use of the dental tool or instrument 10 is desired.

The protective case 54 is preferably at least partially transparent so that the dental tool or instrument 10 is at least partially visible through the protective case 54. The protective case 54 is open, at a open first end thereof, and completely closed at a closed second end thereof. An exterior surface of the protective case 54 is provided with a measurement scale 56, which starts with an initial measurement indicia, e.g., 0.0 cm, at the open first end 60 of the protective case 54, typically ends with an end measurement indicia, e.g. 25 cm, adjacent a closed second end thereof. The shank 38 of the dental tool or instrument 10 supports an adjustable depth indicator 58. The adjustable depth indicator 58 is slidable along the dental tool or instrument 10, by an endodontist prior to use, in order to indicate a desired depth of insertion of the working end of the dental tool or instrument 10 into the desired root canal.

Figure 16:
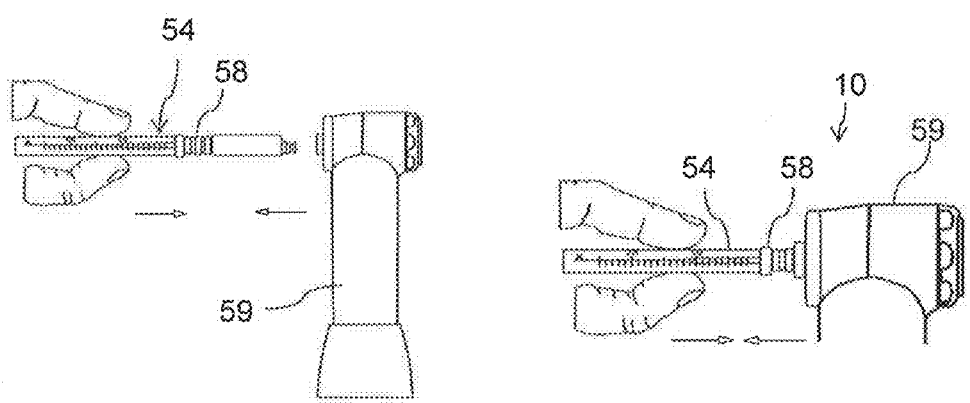
FIG. 16 diagrammatically shows a typical process for attaching the dental tool or instrument to a rotatory tool.
Figure 16A:
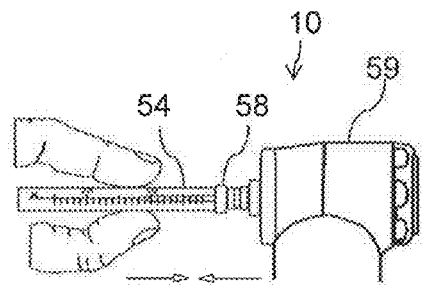
FIG. 16A diagrammatically shows the dental tool or instrument attached to a rotatory tool while the dental tool or instrument is still contained within the protective case.
Figure 16B:
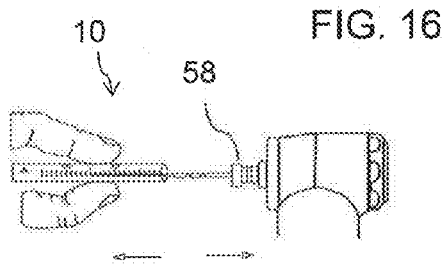
FIG. 16B diagrammatically shows the dental tool or instrument, attached to a rotatory tool, following partial withdrawn of the dental tool or instrument from the protective case.
Figure 16C:
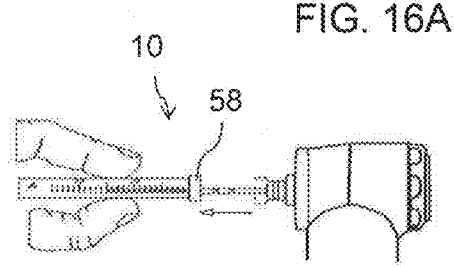
FIG. 16C diagrammatically shows adjustment of the adjustable depth indicator along the dental tool or instrument, once the dental tool or instrument is partially withdrawn from the protective case.

Once an endodontist determines the depth of the root canal of the tooth of the patient to be treated, the endodontist attaches the drive coupling 55 to a suitable conventional rotary tool 59 (see FIGS. 16 and 16A) for driving the dental tool or instrument 10, during use, at a desired rotational speed, e.g., 900±100 rpm for example. Once the exposed end of the drive coupling 55 is securely affixed to the rotary tool 59, the endodontist can then partially remove the dental tool or instrument 10, from the protective case 54, a sufficient distance until a portion of the working area 11 of the dental tool or instrument 10, still remaining within the protective case 54, is equal to the predetermined depth of the root canal of the tooth of the patient to be treated (FIG. 16B). Next, the adjustable depth indicator 58 is then slid, by the endodontist, along the dental tool or instrument 10 from the shank 38 toward the opposite working area 11 until the adjustable depth indicator 58 abuts against the open first end 60 of the protective case 54 (FIG. 16C). As a result of such process, the adjustable depth indicator 58 now provides a visual indication to the endodontist, as soon as the adjustable depth indicator 58 is located closely adjacent/abuts with the tooth of the patient to be treated, that the dental tool or instrument 10 is fully and completely inserted into the root canal and should not be inserted any further into the root canal. That is, the adjustable depth indicator 58 functions as a stop indicator for the endodontist during use of the dental tool or instrument 10.

Figure 16D:
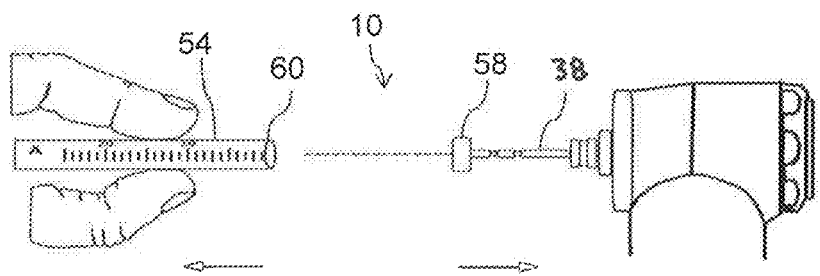
FIG. 16D diagrammatically shows the straightened dental tool or instrument, in its martensitic phase and attached to a rotatory tool, completely withdrawn from the protective case and ready for insertion into a root canal.
Figure 17:
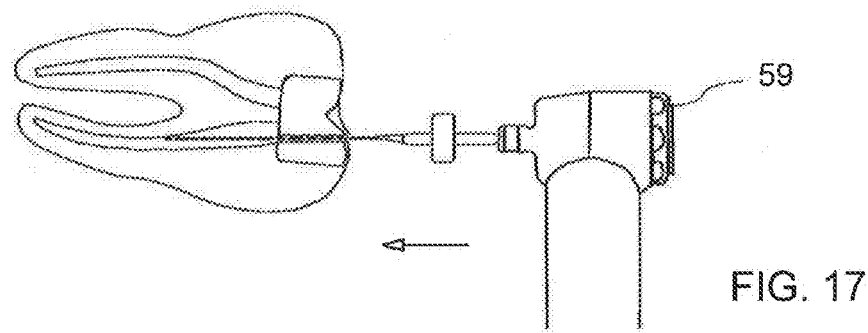
FIG. 17 diagrammatically shows the dental tool or instrument in its martensitic phase immediately upon entering a root canal just prior to the dental tool or instrument reaching its transition temperature.

Prior to completely removing the dental tool or instrument 10 from the protective case 54, the dental tool or instrument 10 is typically cooled, for example, sprayed with a conventional compressed cooling gas or liquid, such as compressed air (not shown). The compressed cooling gas or liquid gradually cools the protective case 54 and such cooling of the protective case 54, in turn, sufficiently cools at least the working area 11 of the dental tool or instrument 10 to a temperature below its final transition temperature so that the working area 11 of the dental tool or instrument 10 can then be temporarily manipulated, molded or conformed into either a generally linear configuration, a slightly curved configuration, a bent configuration or some other desired shape or configuration. For example, the rotary tool 59 may be operated in order to rotate the dental tool or instrument 10, as the dental tool or instrument 10 is being cooled by and located within and by the protective case 54, to permit temporarily deforming of the working area 11 of the dental tool or instrument 10 into the desired linear configuration or shape, e.g., a linear shape as shown in FIG. 16D. Such desired configuration or shape, e.g., linear, curved or bent configuration, generally facilitates insertion of the leading end of the dental tool or instrument 10, by the endodontist, into an inlet opening of the root canal of the tooth to be treated, as generally shown in FIG. 17.

Figure 18:
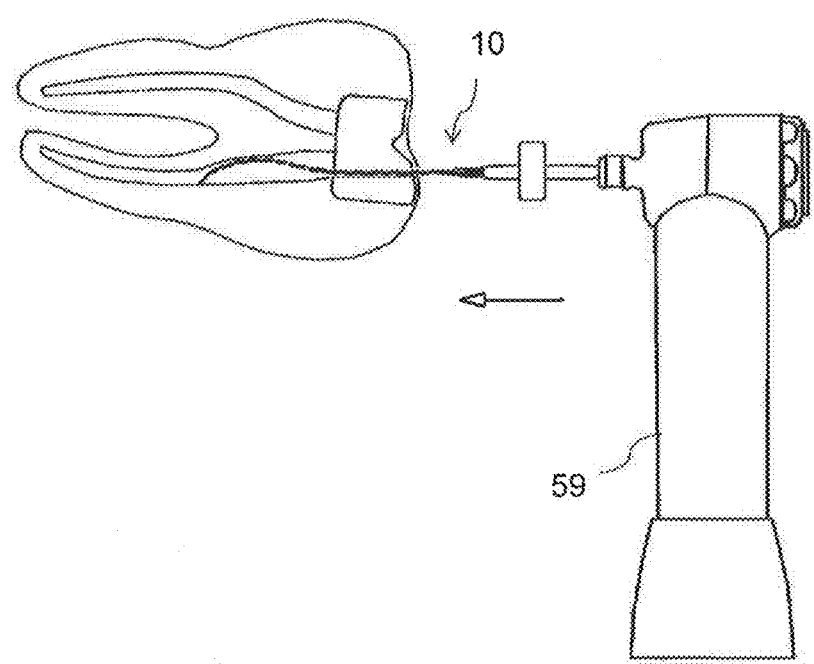
FIG. 18 diagrammatically shows the dental tool or instrument, according to the present invention, operating within an upper region of a typical root canal after transitioning into its austenitic phase and returning to its memorized shape.
Figure 19:
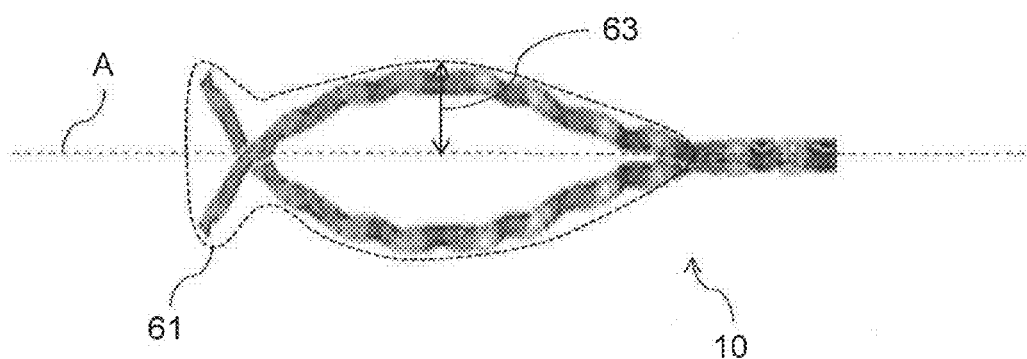
FIG. 19 diagrammatically shows increased volume/radius circumscribed by the at least one bend, undulation, curvature, discontinuity, bulge or protrusion formed in the working area of the dental tool or instrument during rotation thereof.
Figure 20:
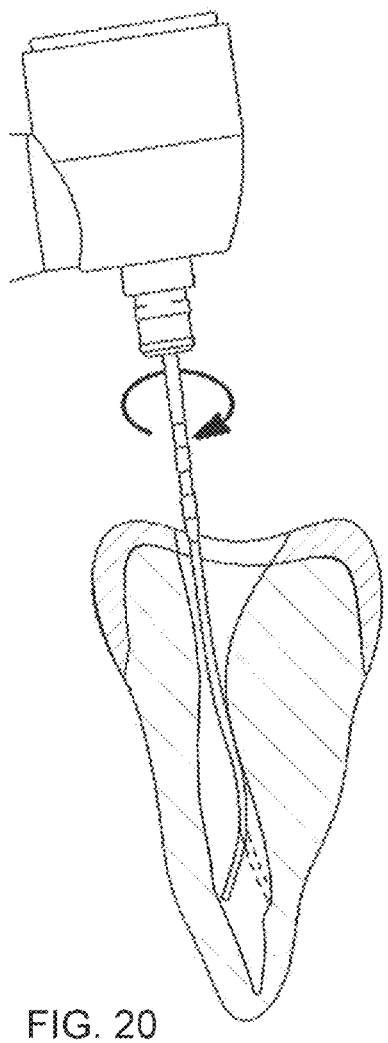
FIG. 20 diagrammatically shows the dental tool or instrument, according to the present invention, operating within a central region of a typical root canal.
Figure 21:
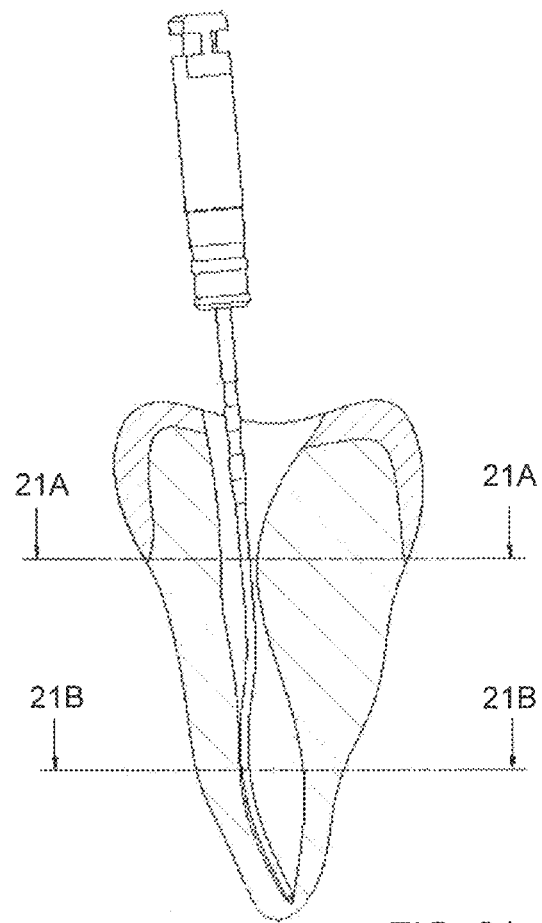
FIG. 21 diagrammatically shows the dental tool or instrument, according to the present invention, operating within a lower region of a typical root canal.
Figure 21A:
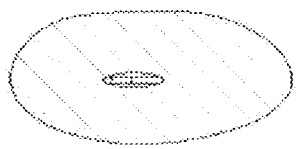
FIG. 21A is a diagrammatical cross section view, along section line 21A-21A, of the root canal shown in FIG. 21.
Figure 21B:
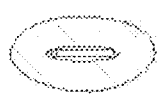
FIG. 21B is a diagrammatical cross section view, along section line 21B-21B, of the root canal shown in FIG. 21.

It is to be appreciated, however, that as soon as a temperature of the dental tool or instrument 10 is heated by the tooth, which is typically at body temperature, the dental tool or instrument 10 instantaneously and automatically transitions from its martensitic phase into its austenitic phase, as shown in FIG. 18, and the dental tool or instrument 10 simultaneously adopts and conforms back into its memorized shape of the at least one protrusion 36. It is to appreciated that the memorized shape is somewhat more rigid, than the pliable martensite phase, and is thus more effective in scraping or removing the pulp from the inwardly facing surface of the root canal of the tooth to be treated, as generally shown in FIGS. 20, 21, 21A and 21B. The at least one protrusion 36, of the dental tool or instrument 10, is highly effective in removing, cleaning and clearing pulp from cylindrical or tubular shaped area and regions of the root canal as well as oval and other non-cylindrical areas and regions of the root canal, which normally do not lend themselves to complete cleaning and removal of pulp by the currently available prior art dental tools.

According to the present invention, the at least one protrusion 36 of the dental tool or instrument 10, when rotated by the rotary tool 59, increases the radius and volume 61 (FIG. 19) encompassed and/or circumscribed by the dental tool or instrument 10. It is to be appreciated that if the dental tool or instrument 10 merely had a linear shape or configuration, the radius or volume 61 circumscribed by the dental tool or instrument 10, when in its austenitic phase, would merely equal the volume defined by the dental tool or instrument 10, as generally shown in FIG. 17. As is apparent from this Figure, it is quite difficult for the endodontist to manipulate the dental tool or instrument 10 so as to completely clean and remove all of the pulp from the inwardly facing surfaces of the root canal, especially in the complex curved and narrowed cross-sections areas of the root canal which typically do not readily lend themselves to complete pulp removal and cleaning.

Due the increased radius and volume of the at least one protrusion 36 of the dental tool or instrument 10, as the dental tool or instrument 10 is rotated by the rotary tool 59, the cutting surface(s) or edge(s) 34 of the at least one protrusion 36 is brought into intimate contact with and scrapes against the inwardly facing surface of the root canal, especially in complex curved and narrowed cross-sections areas of the root canal which typically do not readily lend themselves to complete pulp removal and cleaning. That is, the memorized shape of the at least one protrusion 36 assists with maintaining the cutting surface(s) or edge(s) 34 in constant and intimate contact with the inwardly facing surface of the root canal during use. Such constant and intimate contact with the inwardly facing surface of the root canal continuously occurs during the entire time that the dental tool or instrument 10 is located within the root canal, e.g., constantly as the endodontist gently plunges the dental tool or instrument 10 toward and away from the bottom of the root canal. The increases radius and volume of the at least one protrusion 36 of the dental tool or instrument 10, as it is rotated within the root canal, coupled with the to and fro plunging motion of the endodontist, ensures complete removal of all of the pulp contained within the root canal being treated.

Preferably, the nitirol wire, for use with the present invention, includes 54-57 weight percent nickel and 43-46 weight percent titanium.

After completely removing the dental tool or instrument 10 from the root canal, the dental tool or instrument 10 may either be properly discarded or may possibly be cooled, for example, sprayed with a conventional compressed cooling and sanitizing gas or liquid. The compressed sanitizing and cooling liquid or gas cools at least the working area 11 of the dental tool or instrument 10 to a temperature below its final transition temperature. Similar to when first formed, the working area 11 of the dental tool or instrument 10 can then be temporarily manipulated, molded or conformed into either a generally linear configuration, a slightly curved configuration, a bent configuration or some other desired shape or configuration. Such manipulation generally facilitates insertion of the leading end of the dental tool or instrument 10, by the endodontist, into an inlet opening of a sanitized protective case 54. The dental tool or instrument 10 may then be stored in its martensitic phase until desired for future use.

The present invention is not limited to the embodiments described, but may undergo different modifications or variations. In particular, despite the fact that the variations described are manual and mechanically driven, it is also possible to use ultrasonic vibrations to control the instrument 10. Additionally, depending upon the forms selected, preparation of the root canal may vary. These variations may also be obtained by adaptations in the shape of the metal wire the instrument 10 is made of, the shape possibly being smooth or sharp, round or angular, etc.

The invention claimed is:

1. A method of forming a dental tool or instrument having a memorized shape, the method comprising:
    selecting a nitinol wire having an initial transition temperature below room temperature;
    grinding the nitinol wire to form the dental tool or instrument so as to have a shank, located adjacent a first end, and a working area, with at least one cutting surface, located adjacent an opposite second leading end;
    molding the working area into a molded shape having at least one protrusion formed therein by applying a slight pressure to the working area which is only sufficient to induce the working area of the dental tool or instrument to follow a contour of the at least one protrusion of the mold;
    heating the dental tool or instrument to both:
        a) alter the initial transition temperature of the dental tool or instrument to a final transition temperature of about 90.5±4 degrees Fahrenheit (i.e., 32.5±3 degrees Celsius); and
        b) memorize the molded shape including the at least one protrusion so that the dental tool or instrument will automatically return to the molded shape having the at least one protrusion as soon as the dental tool or instrument is at a temperature at or above the final transition temperature.

2. The method according to claim 1, further comprising:
    heating the dental tool or instrument to a temperature of between about 392 and 707 degrees Fahrenheit (200 and 375 degrees Centigrade) to alter both the initial transition temperature of the dental tool or instrument and memorize the molded shape having the at least one protrusion for a duration of time of between 30 minutes and 240 minutes.

3. The method according to claim 1, further comprising:
    heating the dental tool or instrument to a temperature of between about between 482 and 662 degrees Fahrenheit (250 and 350 degrees Centigrade) to alter both the initial transition temperature of the dental tool or instrument and memorize the molded shape having the at least one protrusion for a duration of time of between 30 minutes and 240 minutes.

4. The method according to claim 1, further comprising:
    heating the dental tool or instrument, for a time of between 30 minutes and 240 minutes, to a temperature which both alters the initial transition temperature of the dental tool or instrument to the final transition temperature and facilitates memorization of the molded shape having the at least one protrusion, when the dental tool or instrument is at a temperature at or above the final transition temperature.

5. The method according to claim 1, further comprising:
    heating the dental tool or instrument, for a time of between 45 minutes and 90 minutes, to a temperature which both alters the initial transition temperature of the dental tool or instrument to the final transition temperature and facilitates memorization of the molded shape having the at least one protrusion, when the dental tool or instrument is at a temperature at or above the final transition temperature.

6. The method according to claim 1, further comprising:
    forming the at least one protrusion to have one of a curved and an arcuate shape which increases at least one of the radius and a volume of the dental tool or instrument when rotated by a rotary tool with the at least one protrusion and the dental tool or instrument defining a plane.

7. The method according to claim 1, further comprising:
    forming the at least one protrusion to have a curved or an arcuate length of between about 1 and 16 mm and a width, measured relative to a longitudinal axis of the dental tool or instrument, of between about 0.1 to about 3.0 mm, without twisting the dental tool or instrument.

8. The method according to claim 1, further comprising:
    memorizing the molded shape having the at least one protrusion by placing the dental tool or instrument mold in a mold having both a negative impression and a positive impression of the at least one protrusion to be formed in at least the working area of the dental tool or instrument;
    applying, via the mold, a pressure of less than a thousand pounds per square to the working area of the dental tool or instrument; and
    heating the dental tool or instrument to a temperature of between about 392 and 707 degrees Fahrenheit (200 and 375 degrees Centigrade) for a duration of time of between 30 minutes and 240 minutes in order to both 1) alter the initial transition temperature of the dental tool or instrument to the final transition temperature and 2) memorizing the molded shape having the at least one protrusion.

9. The method according to claim 8, further comprising:
    of following heating of the mold of the dental tool or instrument, within the mold, rapidly cooling the mold so as to rapidly cool the dental tool or instrument.

10. The method according to claim 9, further comprising:
    rapidly cooling the mold by quenched the mold in a liquid bath so as to rapidly cool the dental tool or instrument.

11. The method according to claim 1, further comprising:
    packaging the dental tool or instrument in a protective case and an exterior packaging which ensures sterility of the dental tool or instrument,
    forming the protective case to be at least partially transparent; and
    providing a measurement scale on a surface of the protective case.

12. The method according to claim 1, further comprising:
    attaching a drive coupling to the shank of the dental tool or instrument to facilitate coupling of the dental tool or instrument to a rotary drive.

13. The method according to claim 1, further comprising:
    providing an adjustable depth indicator on the dental tool or instrument which is slidable along the dental tool or instrument, prior to use, for indicating a desired depth of insertion of a working end of the dental tool or instrument into a desired root canal.

14. The method according to claim 1, further comprising:
    subjecting an exterior surface of the dental tool or instrument to an electropolishing process which smooths any imperfections or deformities in the exterior surface of the dental tool or instrument in order to render the dental tool or instrument more resistant to breakage and/or fatigue during use.

15. A method of forming a dental tool or instrument having a memorized shape, the method comprising:
    selecting a nitinol wire having an initial transition temperature below room temperature;

grinding the nitinol wire to form the dental tool or instrument so as to have a shank, located adjacent a first end, and a working area, with at least one cutting surface, located adjacent an opposite second leading end;

molding the working area into a molded shape having at least one protrusion formed therein by applying a slight pressure to only the working area of the dental tool or instrument which is only sufficient to induce the working area of the dental tool or instrument to follow a contour of the at least one protrusion of the mold but insufficient to permanently deform the working area of the dental tool or instrument;

subjecting an exterior surface of the dental tool or instrument to an electropolishing process to smooth out any imperfections or deformities in the exterior surface of the dental tool or instrument and render the dental tool or instrument more resistant to breakage and/or fatigue during use;

heating the dental tool or instrument to both:
  a) alter the initial transition temperature of the dental tool or instrument to a final transition temperature of about 90.5±4 degrees Fahrenheit (i.e., 32.5±3 degrees Celsius); and
  b) memorize the molded shape which include a linear shank and the at least one protrusion so that the dental tool or instrument will automatically return to the molded shape having the at least one protrusion as soon as the dental tool or instrument is at a temperature at or above the final transition temperature.

* * * * *